US012743779B2

(12) United States Patent
Mirar et al.

(10) Patent No.: US 12,743,779 B2
(45) Date of Patent: Sep. 22, 2026

(54) SYSTEM AND METHODS FOR CARDIAC CYCLE SELECTION

(71) Applicant: GE Precision Healthcare LLC, Waukesha, WI (US)

(72) Inventors: Hani Nozari Mirar, Oslo (NO); Benjamin Strandli Fermann, Oslo (NO)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 107 days.

(21) Appl. No.: 18/781,913

(22) Filed: Jul. 23, 2024

(65) Prior Publication Data

US 2026/0030744 A1 Jan. 29, 2026

(51) Int. Cl.

*G06T 7/00* (2017.01)
*A61B 8/00* (2006.01)
*A61B 8/08* (2006.01)

(52) U.S. Cl.

CPC .......... *G06T 7/0012* (2013.01); *A61B 8/0883* (2013.01); *A61B 8/5223* (2013.01); *G06T 2207/10016* (2013.01); *G06T 2207/20084* (2013.01); *G06T 2207/30048* (2013.01)

(58) Field of Classification Search

CPC . G06T 2207/10016; G06T 2207/20084; G06T 2207/30048; G06T 7/0012; A61B 8/0883; A61B 8/5223; A61B 8/5269

See application file for complete search history.

(56) References Cited

U.S. PATENT DOCUMENTS

| | | | |
|---|---|---|---|
| 8,977,350 | B2 | 3/2015 | Sarkar et al. |
| 10,517,564 | B2 | 12/2019 | Konofagou et al. |
| 2005/0288599 | A1 | 12/2005 | MacAdam et al. |

(Continued)

FOREIGN PATENT DOCUMENTS

WO 2022243178 A1 11/2022

OTHER PUBLICATIONS

Kotecha, D. et al., "Is echocardiography valid and reproducible in patients with atrial fibrillation? A systematic review," Europace, vol. 19, No. 9, Sep. 1, 2017, 12 pages.

(Continued)

*Primary Examiner* — Carolyn A Pehlke
(74) *Attorney, Agent, or Firm* — McCoy Russell LLP

(57) ABSTRACT

Methods and systems are provided for identifying cardiac cycles for evaluating left ventricle function using only image data. In one example, a method includes obtaining a sequence of medical image frames of a heart of a patient over a plurality of cardiac cycles, wherein each medical image frame depicts the same apical view of the heart, using a timing model to generate an output that is useable to label each frame of the sequence by cardiac cycle subphase and using the output to determine the suitability of each cardiac cycle for performing an automated measurement. The method may further include using the suitability of each cycle to determine if an automated measurement should be performed on each cycle, where automated measurements are performed on medical image frames corresponding to suitable cycles and automated measurements are not performed on medical image frames corresponding to unsuitable cycles.

19 Claims, 10 Drawing Sheets

(56) References Cited

U.S. PATENT DOCUMENTS

| | | | | |
|---|---|---|---|---|
| 2014/0163404 | A1* | 6/2014 | Reichman | A61B 5/0295 600/506 |
| 2017/0215807 | A1 | 8/2017 | Lundback et al. | |
| 2017/0224239 | A1 | 8/2017 | Ng | |
| 2019/0099162 | A1* | 4/2019 | Keshet | G06T 7/0016 |
| 2021/0082112 | A1* | 3/2021 | Li | G06T 7/0012 |
| 2021/0407095 | A1* | 12/2021 | Shao | G06T 7/11 |
| 2024/0127432 | A1* | 4/2024 | Groth | G06V 10/82 |
| 2024/0293100 | A1* | 9/2024 | Olivier | A61B 8/0883 |

OTHER PUBLICATIONS

Fermann, B. et al., "Cardiac Valve Event Timing in Echocardiography Using Deep Learning and Triplane Recordings," IEEE Journal of Biomedical and Health Informatics, vol. 28, No. 5, May 2024, 10 pages.

* cited by examiner

SYSTEM AND METHODS FOR CARDIAC CYCLE SELECTION

TECHNICAL FIELD

Embodiments of the subject matter disclosed herein relate to medical imaging, and more particularly, to selecting images of a cardiac cycle for evaluating left ventricle systolic function.

BACKGROUND

Medical imaging, such as ultrasound, may be used to non-invasively probe the internal structures of a body of a patient and produce a corresponding image. Medical images of the internal structures may be saved for later analysis by a clinician to aid in diagnosis and/or displayed on a display device in real time or near real time. In some examples, computerized tools may be employed to identify internal structures, provide suggested diagnosis, perform automated measurements, and the like.

SUMMARY

In an embodiment, a method includes obtaining a sequence of medical image frames of a heart of a patient over a plurality of cardiac cycles, each medical image frame in the sequence depicting a same apical view of the heart; determining, based on output from a timing model trained to generate output usable to label each frame of the sequence by cardiac cycle subphase, a suitability of each cardiac cycle for performing an automated measurement; determining, based on the suitability of each cardiac cycle, that a first cardiac cycle is not suitable, and in response, not performing the automated measurement on medical image frames of the sequence that correspond to the first cardiac cycle; and determining, based on the suitability of each cardiac cycle, that a second cardiac cycle is suitable, and in response, performing the automated measurement on medical image frames of the sequence that correspond to the second cardiac cycle.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
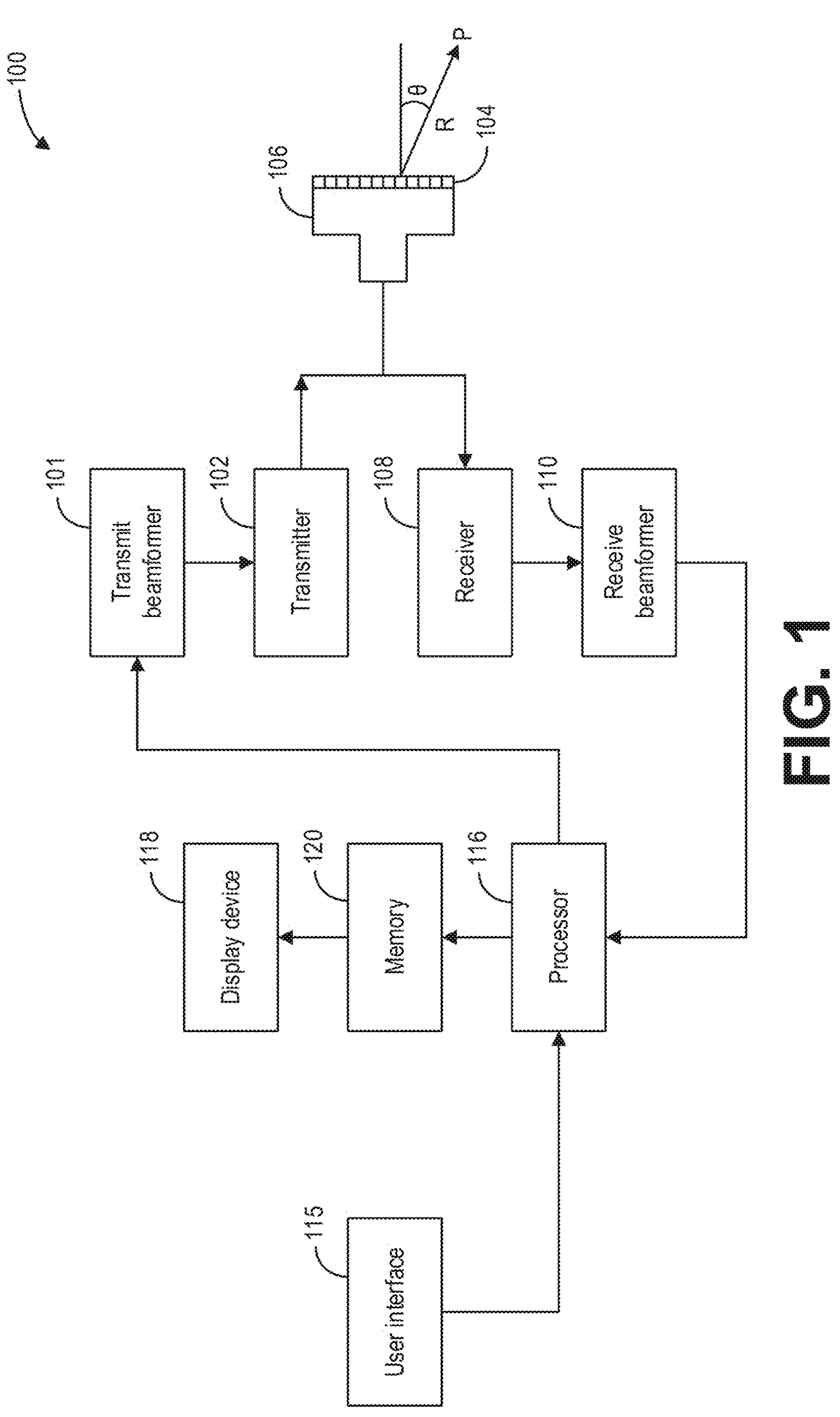
FIG. 1 shows a block diagram of an embodiment of an ultrasound imaging system.

Medical images, such as ultrasound images, may be used to diagnose or rule out patient conditions in a non-invasive manner. To facilitate analysis of a patient condition, computerized tools may be applied to medical images in order to provide automated or semi-automated measurements of anatomical features, identify or characterize tissue, or even suggest diagnoses of patient conditions. As an example, during echocardiograms where a patient's heart is imaged with ultrasound, Automated Function Imaging (AFI) may be applied to perform 2D speckle tracking to measure deformation (strain) of the myocardial wall. However, a full cardiac cycle may need to be captured to fully analyze cardiac cycle and assess the function of the left ventricle (LV). As another example, function of the LV may be assessed using ejection fraction, which is the percentage of blood that is pumped out of the filled LV during each cardiac cycle. Ejection fraction may be assessed based on ultrasound images of the heart. In patients with atrial fibrillation (AFib), there may be significant variations between cardiac cycles. In some examples, parts of the cardiac cycle may be shortened or omitted during a fibrillation. The current approach to obtain suitable cycle parameters (e.g., LV function measurements such as strain or ejection fraction) from a patient with AFib may involve storing and recording ultrasound data from between five and ten cardiac cycles. Cycle parameters may be determined by averaging the parameters measured over all of the stored cycles. This approach stores a relatively large amount of data, and may produce inaccurate parameter values by including cardiac cycles that do not represent the function of the patient's heart in the average. In the example that the ejection fraction of the left ventricle is being assessed, a cardiac cycle that is missing one or more subphases may be unsuitable for use in determining the ejection fraction because the left ventricle may not fully fill or empty due to atrial fibrillation.

Thus, according to embodiments disclosed herein, suitable cycles to assess left ventricle function may be automatically selected based on image data. The method may include capturing a video of the heart during a plurality of cardiac cycles via ultrasound. A timing model may be applied to the video to identify which medical image frames of the video correspond to each subphase of the cardiac cycle. Each cardiac cycle can then be assessed, via the labeled medical image frames imaging that cardiac cycle, to determine if the cardiac cycle is normal based on the timing and presence of the subphases of the cardiac cycle. Cardiac cycles may be assessed as they are collected, and only suitable cycles may be saved. In some examples, only three cycles may be saved. Compared to previous methods that save 5-10 cycles, this method demands less memory. Additionally, evaluating cycles as they are collected and stopping collection once three suitable cycles have been collected may take less time than collecting 5-10 cycles and analyzing the cycles after collection. In some examples, identifying and analyzing suitable cycles according to the method above may use less processing power than previous methods to automatically identify and analyze the subphases of the cardiac cycle from imaging data. The method described above relies on the ultrasound video of the heart and does not require an electrocardiogram (ECG) to be performed. The method described above may be more accurate than an ECG in identifying the subphases included during a cardiac cycle because each image contains more information than is provided by the V2 lead of the ECG.

Figure 3:
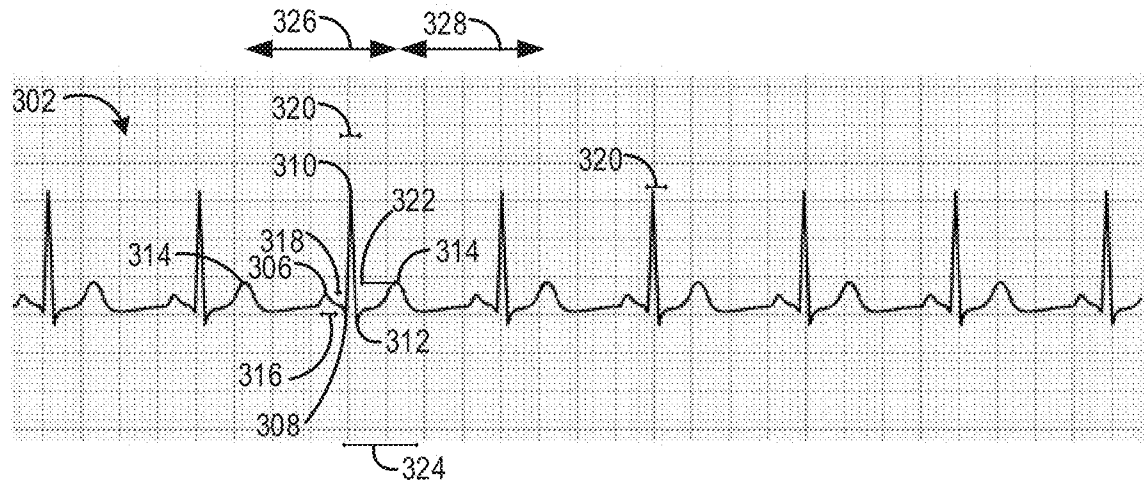
FIG. 3 is an electrocardiogram displaying normal heart function and an electrocardiogram of a heart experiencing atrial fibrillation.
Figure 3:
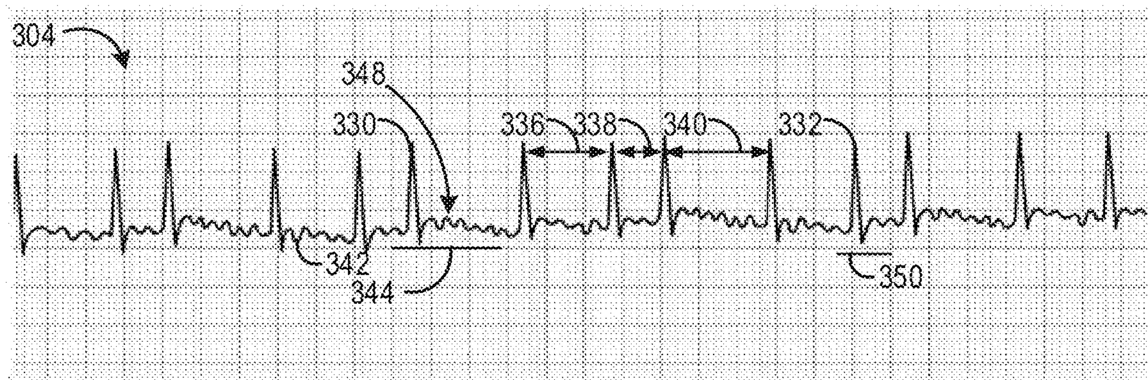
Figure 4:
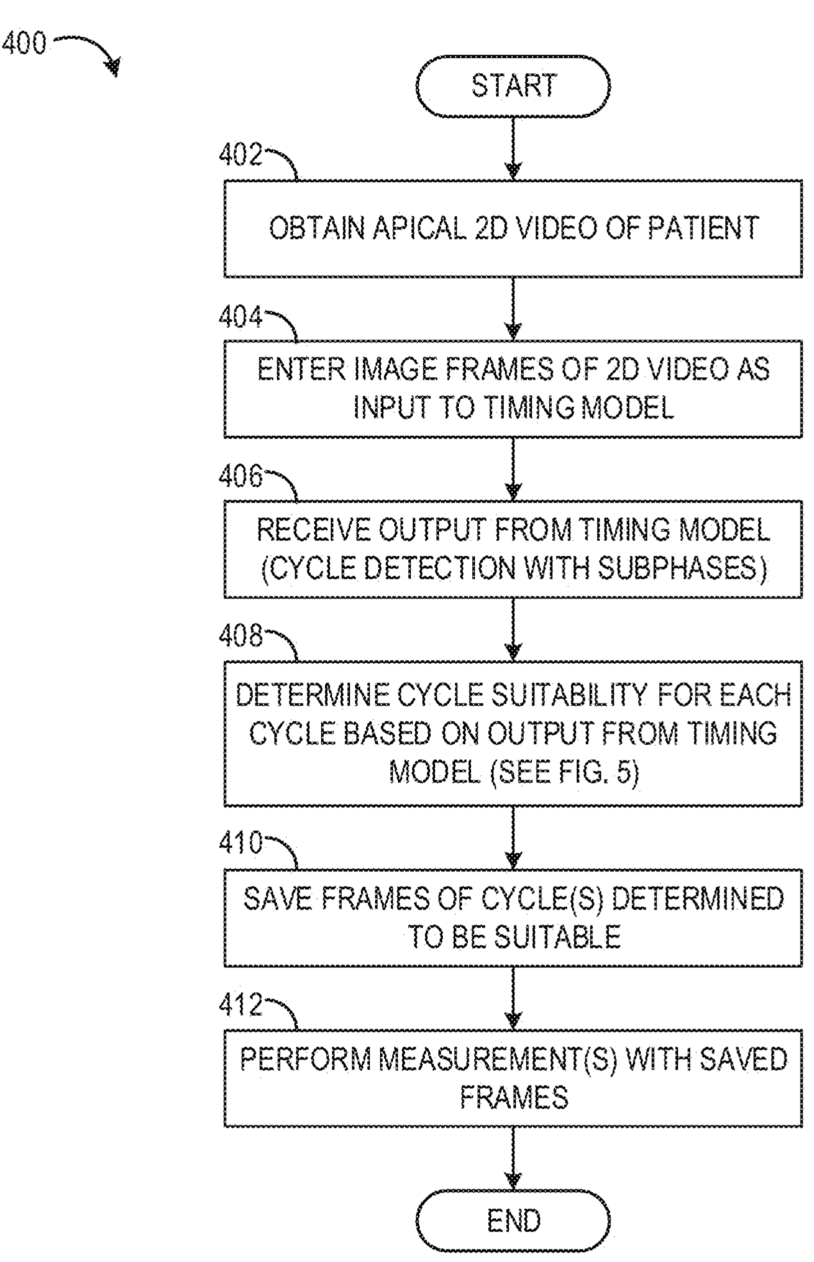
FIG. 4 is a flowchart illustrating a method for selecting and storing suitable cardiac cycles based on image data and output from a timing model.
Figure 5:
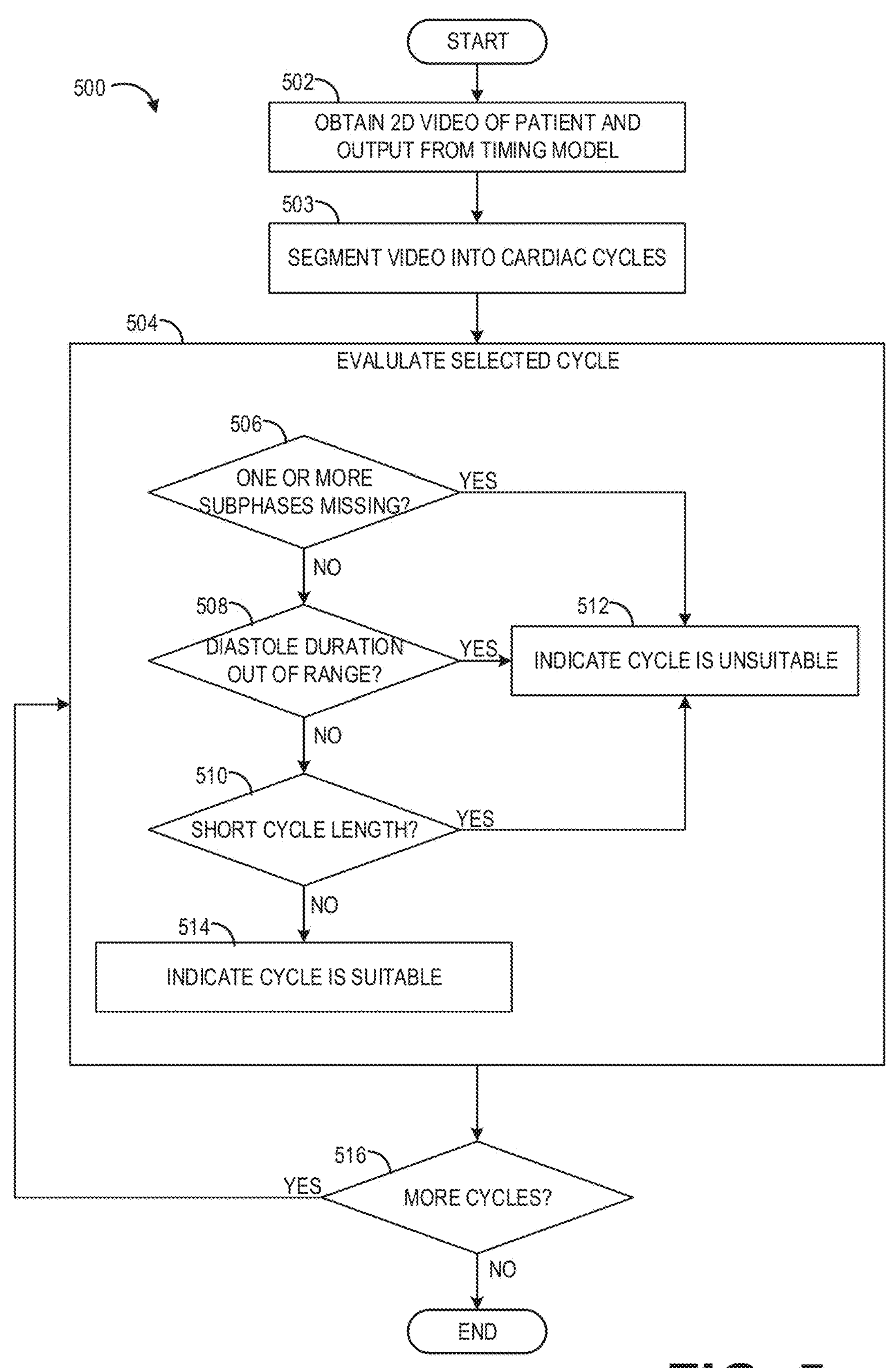
FIG. 5 is a flowchart illustrating a method to determine the suitability of cardiac cycles based on the output of the timing model.
Figure 6:
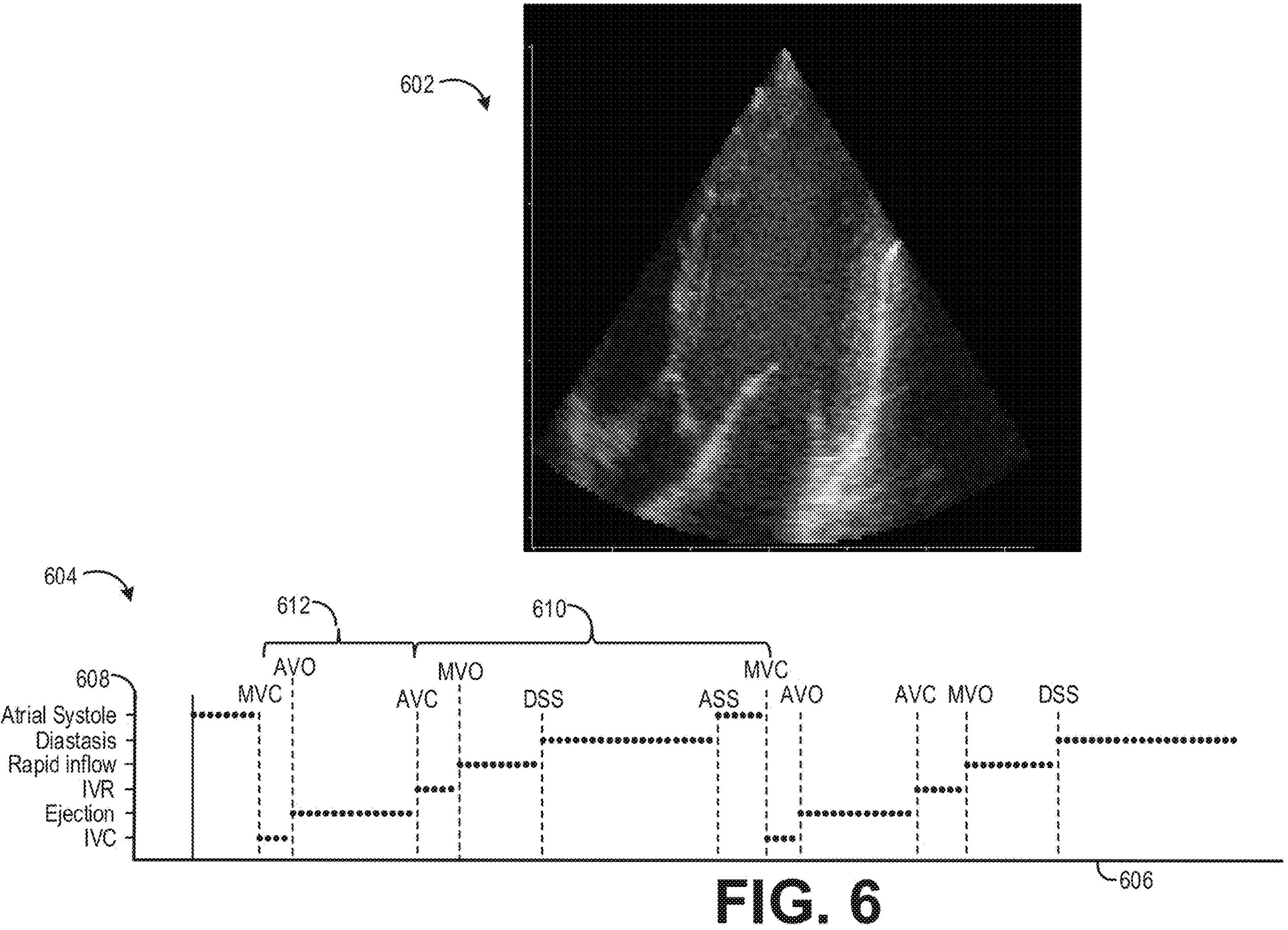
FIG. 6 is an example of a video of a cardiac cycle with medical image frames labeled according to the subphase of the cardiac cycle.
Figure 7:
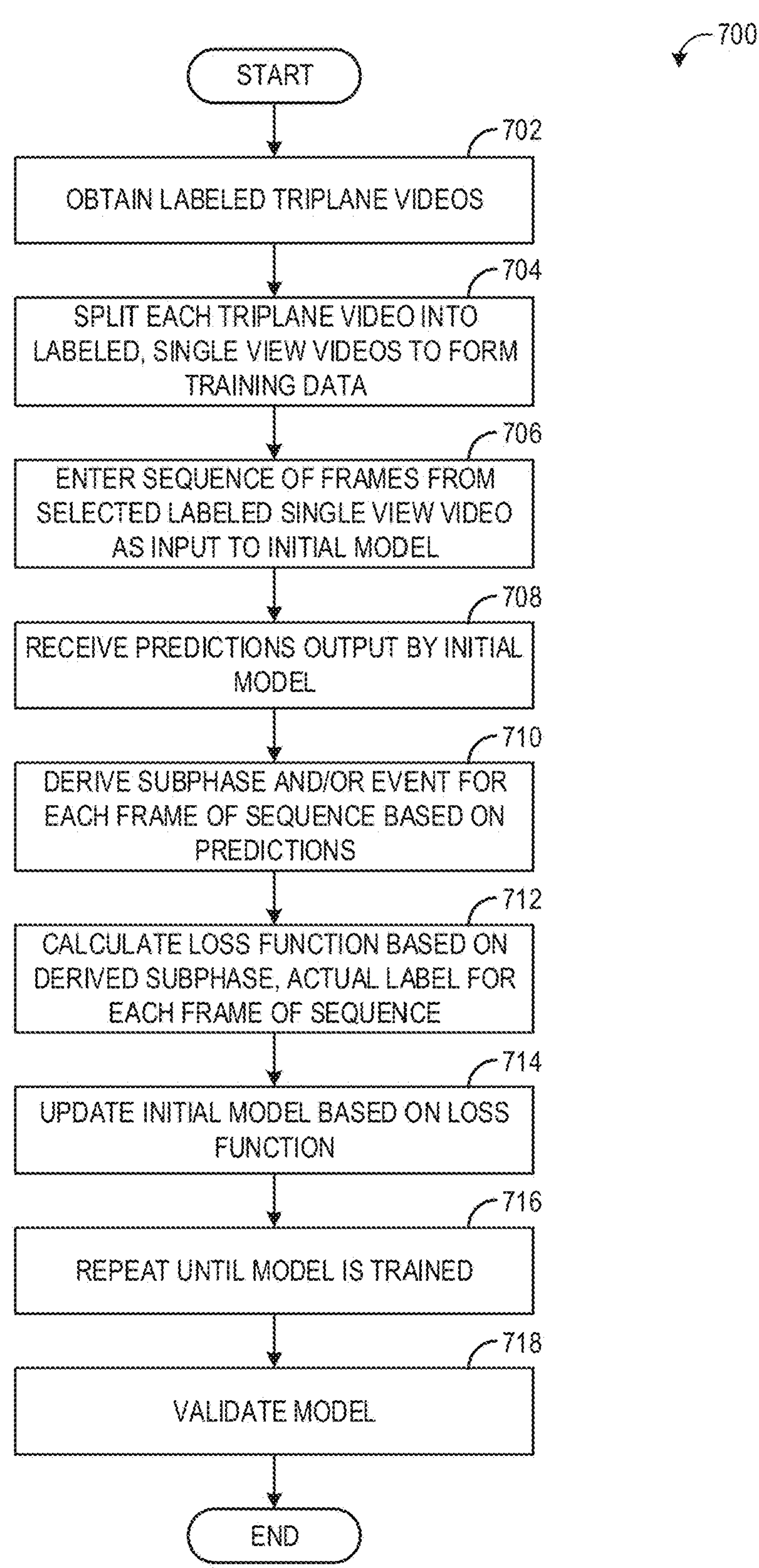
FIG. 7 is a flowchart of a method to train a timing model.
Figure 8:
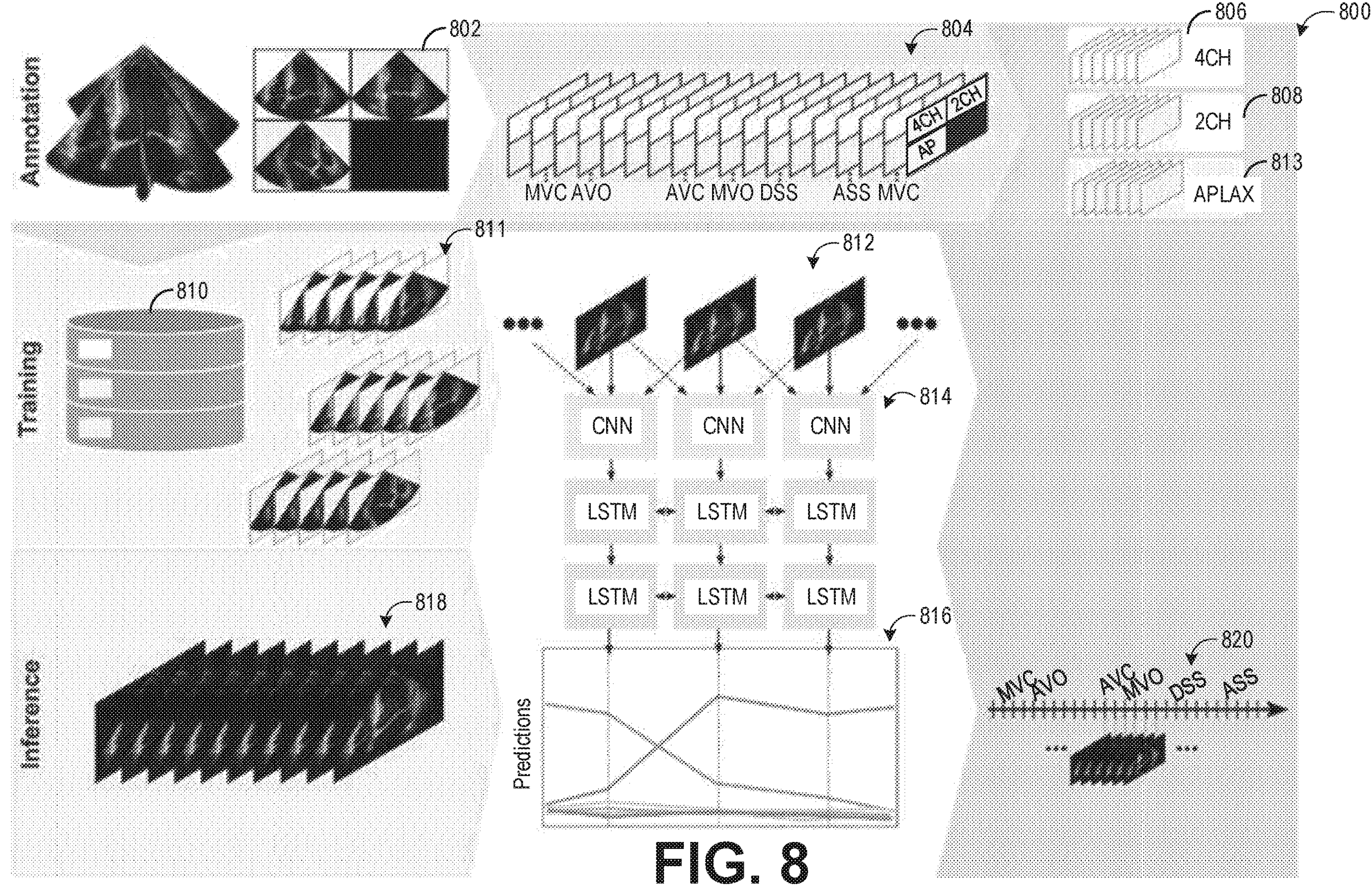
FIG. 8 is a schematic diagram of a method for training a timing model.
Figure 9:
FIG. 9 is a first set of plots showing the frame labels used by a timing model and prediction curves output by the timing model during training.
Figure 9:
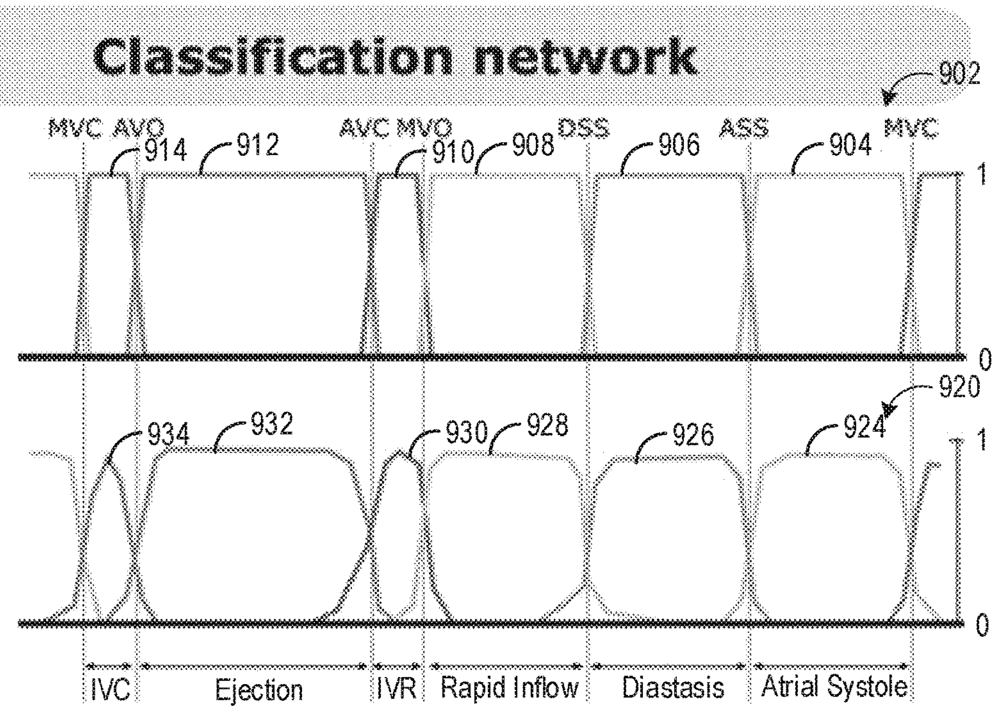
Figure 10:
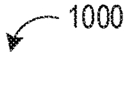
FIG. 10 is a second set of plots showing the frame labels used by a timing model and prediction curves output by the timing model during training.
Figure 10:
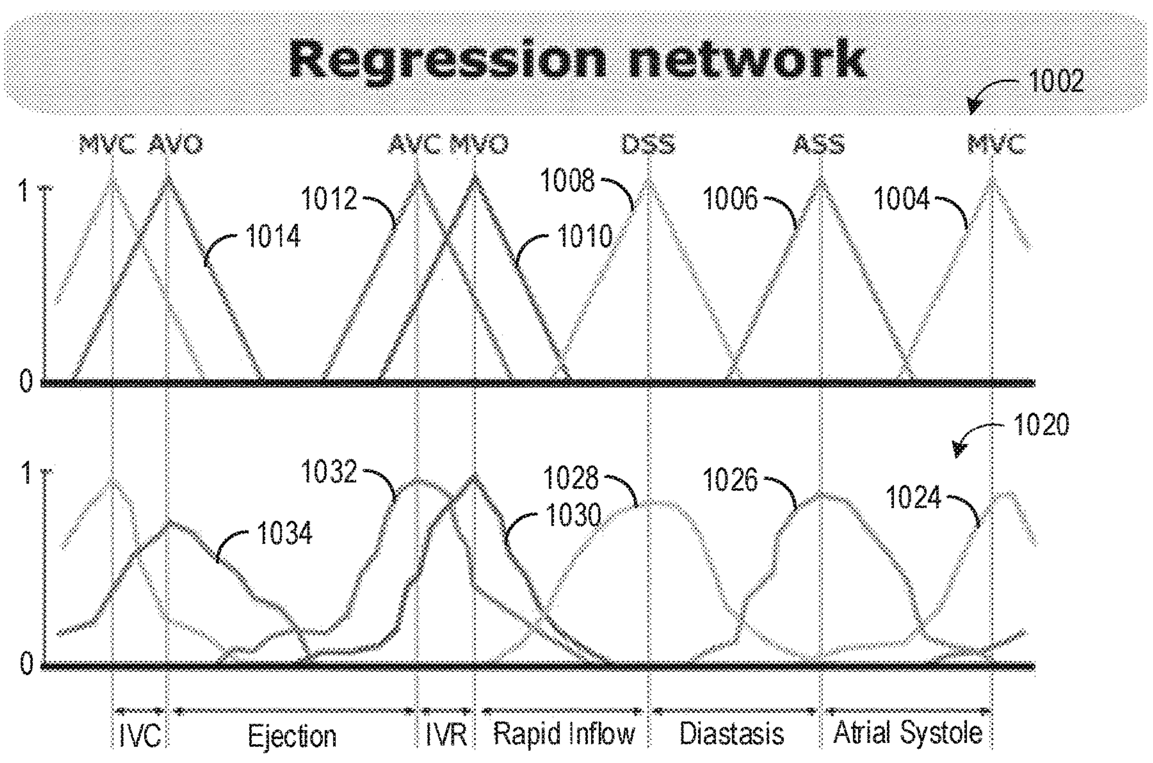

An example ultrasound system including an ultrasound probe, a display device, and an imaging processing system are shown in FIG. 1. Via the ultrasound probe, ultrasound data may be acquired and ultrasound videos may be displayed on the display device. The ultrasound videos may be processed by an image processing system, such as by the image processing system of FIG. 2, configured to execute machine readable instructions that may segment the ultrasound video into sets of medical image frames, each set corresponding to a cardiac cycle, label the medical image frames of the ultrasound video by subphase of the cardiac cycle using a timing model, determine a suitability of each set of medical images frames of the video for performing an automated measurement based on the labeled subphases, and save the suitable sets of medical image frames for performing the measurement. FIG. 3 shows example ECG traces of a standard cardiac cycle compared to the cardiac cycle of a heart with AFib. FIG. 4 shows an example method for processing a video of a patient heart to segment the video into subphases of the cardiac cycle, save images corresponding to suitable cycles, and perform measurements on the images of the suitable cycles. FIG. 5 shows an example method for executing a decision logic for determining which cycles are suitable for use in automatic measurements. FIG. 6 shows an example of medical image frames of an ultrasound video labeled by the subphases of a cardiac cycle. FIG. 7 shows a flowchart of a method to train a timing model including inputting a three ultrasound views of a heart beating, using an initial timing model to label each frame with a subphases of the cardiac cycle, then comparing the subphase labels output by the timing model with subphase labels assigned by experts and updating the timing model. FIG. 8 is a schematic representation of the method described with respect to FIG. 7. FIGS. 9-10 show the frame labels used by a timing model and prediction curves output by the timing model during training.

The timing model disclosed herein may be applied to medical image frames in order to identify subphases of the cardiac cycle in the medical image frames and select medical image frames obtained during one or more target cycles based on the identified subphases to be saved for further processing, such as determining the ejection fraction of the left ventricle. An example ultrasound imaging system usable to generate medical images that can be input to the timing model as disclosed herein is shown in FIG. 1. However, it is to be appreciated that an ultrasound imaging system is presented herein as an example medical imaging system and that the timing model may be implemented with other medical images without departing from the scope of this disclosure, such as computed tomography (CT) images, magnetic resonance (MR) images, x-ray images, visible light images, and the like.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic wave. In this way, transducer elements 104 may convert electronic transmit signals into acoustic transmit beams.

After the transducer elements 104 of the probe 106 emit pulsed ultrasonic signals into a body (of a patient), the pulsed ultrasonic signals reflect from structures within an interior of the body, like blood cells or muscular tissue, to produce echoes that return to the transducer elements 104. The echoes are converted into electrical signals, or ultrasound data, by the transducer elements 104 and the electrical signals are received by a receiver 108. The electrical signals representing the received echoes are passed through a receive beamformer 110 that outputs ultrasound data.

The echo signals produced by transmit operation reflect from structures located at successive ranges along the transmitted ultrasonic beam. The echo signals are sensed separately by each transducer element and a sample of the echo signal magnitude at a particular point in time represents the amount of reflection occurring at a specific range. Due to the differences in the propagation paths between a reflecting point P and each element, however, these echo signals are not detected simultaneously. Receiver 108 amplifies the separate echo signals, imparts a calculated receive time delay to each, and sums them to provide a single echo signal which approximately indicates the total ultrasonic energy reflected from point P located at range R along the ultrasonic beam oriented at the angle θ.

The time delay of each receive channel continuously changes during reception of the echo to provide dynamic focusing of the received beam at the range R from which the echo signal is assumed to emanate based on an assumed sound speed for the medium.

Under direction of processor 116, the receiver 108 provides time delays during the scan such that steering of receiver 108 tracks the direction θ of the beam steered by the transmitter and samples the echo signals at a succession of ranges R so as to provide the time delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the transducer elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the real RF (radio-frequency) data and generates complex data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of less than optimal or low resolution, especially for areas of greater depth.

Figure 2:
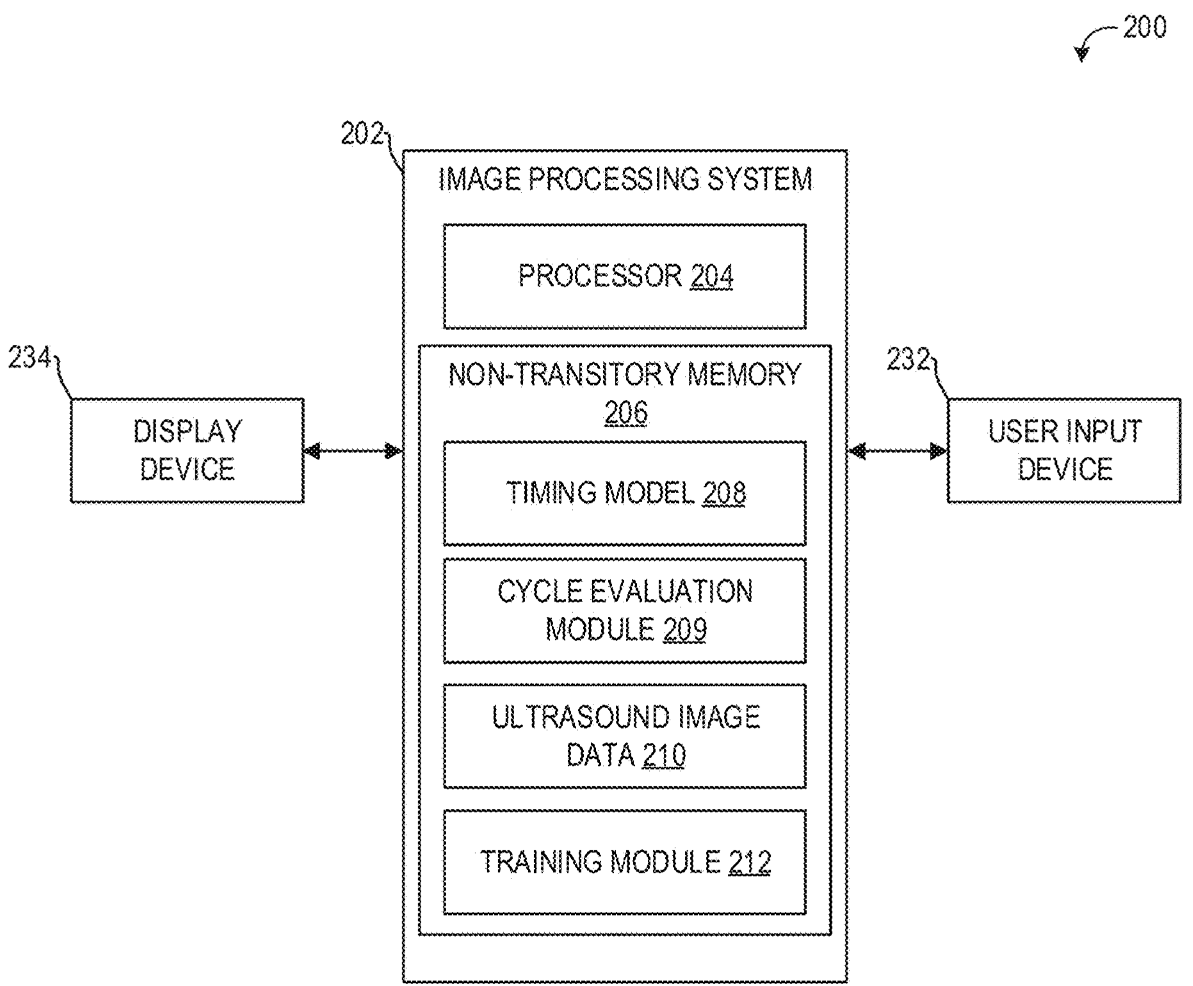
FIG. 2 is a block diagram showing an example image processing system.

Referring to FIG. 2, an image processing system 202 is shown, in accordance with an embodiment of the disclosure. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing system 202 is included in a device (e.g., edge device, server, etc.) communicably coupled to the ultrasound imaging system via wired and/or wireless connections. In some embodiments, at least a portion of image processing system 202 is included in a separate device (e.g., a workstation), which can receive images from the ultrasound imaging system or from a storage device which stores the images/data generated by the ultrasound imaging system. Image processing system 202 may be operably/communicatively coupled to a user input device 232 and a display device 234. In one example, the user input device 232 may comprise the user interface 115 of the ultrasound imaging system 100, while the display device 234 may comprise the display device 118 of the ultrasound imaging system 100.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store a timing model 208, a cycle evaluation module 209, ultrasound image data 210, and a training module 212. Timing model 208 may include one or more machine learning models, such as deep learning networks (e.g., convolutional neural networks and/or long short-term memory (LSTM) recurrent neural networks), comprising a plurality of weights and biases, activation functions, loss functions, gradient descent algorithms, and instructions for implementing the one or more deep neural networks to process input ultrasound videos of one or more cardiac cycles in order to identify which medical image frames within an ultrasound video belong to each subphase of the cardiac cycle. The timing model may be trained using training data comprised of ultrasound videos of hearts from an apical triplane view including 4CH, 2CH and APLAX views recorded simultaneously. The training data may be labeled by experts in the field to identify the medical image frames of the videos that correspond to events that signal transitions between each subphase of the cardiac cycle, such as the opening or closure of valves in the heart. The timing model may include a classification network or a regression network, which may each include a convolutional layer and an LSTM layer. Additional details about the timing model, including training of the timing model and example architectures of the timing model, are provided below with respect to FIGS. 7-10. Timing model 208 may include trained and/or untrained neural networks and may further include training routines, or parameters (e.g., weights and biases), associated with one or more neural network models stored therein. As will be explained herein, cycle evaluation module 209 may be configured to determine, based on the output of the timing model 208, whether one or more cardiac cycles captured in the ultrasound videos are suitable for performing one or more automatic measurements, such as evaluation of LV function.

Ultrasound image data 210 may include medical image frames of ultrasound videos captured by the ultrasound imaging system 100 of FIG. 1 or another ultrasound imaging system. The ultrasound image data 210 may include 2D images and/or 3D volumetric data, from which 2D images/slices may be generated. The ultrasound image data 210 may include B-mode images, Doppler images, color Doppler images, M-mode images, etc., and/or combinations thereof. In some embodiments, ultrasound image data 210 may store ultrasound images and ground truth output in an ordered format, such that each ultrasound image is associated with one or more corresponding ground truth outputs. However, in examples where training module 212 is not disposed at the image processing system 202, the images/ground truth output usable for training the timing model 208 may be stored elsewhere.

Non-transitory memory 206 may further include training module 212, which comprises instructions for training one or more of the machine learning models stored in timing model 208. In some embodiments, the training module 212 is not disposed at the image processing system 202. The timing model 208 thus includes trained and validated network(s).

In some embodiments, the non-transitory memory 206 may include components included in two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, or to request cycle selection be performed on an ultrasound video using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Thus, the image processing system 202 may be configured to take an ultrasound video of a one or more cardiac cycles taken from one of three possible views (e.g., 2-chamber (2CH), 4-chamber (4CH), and apical long axis (APLAX)) and input the video into the timing model 208. The timing model 208 may identify and label the medical image frames within the videos that signal the transitions between subphases of the cardiac cycle (e.g., the frames that signal the start of a new subphase). The transitions between subphases are discussed in more detail below, but correspond to the opening and closure of valves during the cardiac cycle. The medical image frames between the transition medical image frames may be labeled as belonging to a subphase of the cardiac cycle defined as the period of time between two events such as the opening and closure of cardiac valve. The timing model 208 may further output a respective probability, for each frame of the video, that the frame belongs to each subphase. Each frame may be labelled with the subphase that the frame has the highest probability of belonging to. The timing model 208 may be trained according to the following method. Experts in the field may prepare training data (e.g., a set of training videos) for the timing model 208 wherein they identify which medical image frames of the set of training videos include a transition event and which medical image frames belong to each subphase of the cardiac cycle. A subset of the training data may be withheld from use in training the timing model 208 to evaluate the effectiveness of the timing model 208. The training data may be input to the timing model 208, which may output predictions of which subphase each frame of each training video depicts. A loss function may be calculated based on the comparison between the subphases determined by the timing model 208 and the subphases determined by the experts who labeled the videos. The timing model 208 may be updated based on the loss function.

The cycle evaluation module 209 may include decision logic that may be applied to the output of the timing model 208 to determine the suitability of a cardiac cycle identified by the timing model 208 for use in measuring metrics of left-ventricle function. The decision logic for determining the suitability of a cycle may be described in more detail with respect to FIG. 5. A suitable cycle for automatic measurement may include all subphases of the cardiac cycle, have a diastole that is longer than systole, and have a cycle length that is not shorter (or significantly shorter) than an average cycle length. These metrics are typical of a cardiac cycle that is unaffected by AFib, as AFib is known to interrupt cardiac cycles, making a cardiac cycle short, skipping phases in the cardiac cycle and impacting the length of diastole compared to systole. These metrics can be determined based on the output of the timing model 208, which labels each frame by cardiac subphase. The presence and duration of each subphase (and the duration of systole and diastole) may be determined from the number of each frames corresponding to each subphase.

FIG. 3 shows a first ECG graph 302 of a normal heart compared to a second ECG graph 304 of a heart with AFib. Each ECG graph represents the amplitude of electrical activity of the heart along a vertical axis and the passage of time along a horizontal axis. A cardiac cycle typically begins with the depolarization of the sinus node located in the right atrium of the heart. The depolarization spreads as a wave through the myocardium to the left atrium. The wave of depolarization is then delayed for a small portion of time by the atrioventricular node before being passed to the left and right ventricles simultaneously to trigger them to contract simultaneously. After the myocardium of the heart has completely depolarized, it must repolarize over time before another cardiac cycle can begin. In an ECG, one or more electrodes are placed on a patient's skin to measure the wave of depolarization. When a wave of depolarization travels towards an electrode, the ECG registers a positive change in amplitude and when the wave of depolarization travels away from an electrode, the ECG registers a negative change in amplitude.

The first ECG graph 302 displays features of an ECG associated with a normal cardiac cycle. The cardiac cycle may begin with a P-wave 306. The P-wave 306 represents the combined electrical depolarization of both the left atrium and the right atrium of the heart as initiated by the sinoatrial node, and may be identified as a small positive deflection in the amplitude of the first ECG graph 302. The P-wave 306 typically occurs before a QRS complex 320. A PR segment 318 represents the time delay between atrial depolarization and ventricular depolarization, seen on the first ECG graph 302 as the time between the end of the P-wave 306 and the beginning of the QRS complex 320. A PR interval 316 is the time between the start of the P-wave 306 and the start of the Q-wave 308 and may also be useful in assessing the delay between the P-wave 306 and the Q-wave 308.

The QRS complex 320 represents the depolarization of both ventricles and includes a Q-wave 308, an R-wave 310 and an S-wave 312. The Q-wave 308 may be identified as a small, sharp negative deflection immediately prior to the large, sharp positive deflection that is the R-wave 310. The R-wave 310 is immediately followed by a small, sharp negative deflection that is the S-wave 312. The duration of the QRS complex 320 is the time between the beginning of the Q-wave 308 and the end of the S-wave 312 and may be assessed to analyze the function of the heart. Likewise, the duration of the Q-wave 308, R-wave 310, and S-wave 312 may be individually assessed for irregularities. The QRS complex 320 may be followed by a T-wave 314.

The T-wave 314 is a positive deflection in the first ECG graph 302 that represents the repolarization of the myocardium. An ST segment 322 may be measured between the end of the S-wave 312 and the peak of the T-wave 314. The ST segment 322 may represent the delay between the depolarization of the ventricles and the repolarization of the myocardium. There is also a QT interval 324 that represents the amount of time between the start of the Q-wave 308 and the end of the T-wave 314. In a normal heart rhythm, each cardiac cycle follows the previous one at a relatively constant interval, giving rise to a steady and predictable heart rate. A first cardiac cycle may have a first duration 326 shown next to a cardiac cycle with a second duration 328. The first duration 326 is approximately equal to the second duration 328. This allows for consistent blood flow and lessens the impact of selecting a non-suitable cardiac cycle when assessing LV function.

The cardiac cycle may be split into several steps that may correspond to some features of the waves of the ECG. The cardiac cycle may begin with ventricular diastole, indicated by the T-wave 314, followed by ventricular atrial systole, indicated by the P-wave 306, and ventricular systole, indicated by the QRS complex 320.

The cardiac cycle may be split into two phases: systole and diastole. Systole is a phase during which the left ventricle contracts to eject blood from the left ventricle and includes two subphases, isovolumetric contraction (IVC) and ejection. Diastole is a phase including four subphases: isovolumetric relaxation (IVR), rapid inflow, diastasis, and atrial systole. During IVC, the pressure within the LV increases until the aortic valve opens, at which point ejection begins. During ejection, blood is ejected through the aortic valve. Ejection ends when the aortic valve is closed. Following ejection is IVR, wherein the pressure within the left ventricle decreases until the mitral valve opens. Once the mitral valve opens, the rapid inflow stage begins and blood rapidly enters the left ventricle. The rapid inflow stage ends when the anterior mitral leaflet stops its movement towards the left atrium after opening, beginning diastasis. During diastasis, blood flow through the mitral valve nearly stops. Diastasis is ended by the anterior mitral leaflet moving towards the LV and atrial systole begins. During atrial systole, the atria contract and blood flows into the LV. Atrial systole ends when the mitral valve closes. As disclosed herein, the subphases within the cardiac cycle can be identified by imaging the valves included within the heart in order to identify events that signal a new subphase has begun. The events include mitral valve closure (MVC), aortic valve opening (AVO), aortic valve closure (AVC), mitral valve opening (MVO), atrial systole start (ASS), and diastasis start (DSS).

The time between AVC and MVO is the IVR subphase. Rapid inflow is the period of time between MVO and DSS. Diastasis is the period of time between DSS and ASS. The time between ASS and MVC is atrial systole. The period of time between AVC and MVC is considered systole. The period of time between MVC and AVO is the IVC subphase. The period of time between AVO and AVC is the ejection subphase. The period of time between MVC and AVC is considered diastole.

The second ECG graph 304 of a heart with atrial fibrillation is shown below the first ECG 302 graph of a normal heart. While the normal heartbeat is characterized by heartbeats occurring at approximately a constant interval, the heart with AFib is shown beating at irregular intervals. In atrial fibrillation, the atria beat irregularly and out of coordination with the ventricles, leading to a rapid and irregular heart rate. This results in beat-to-beat variations with some cycles being shorter and others longer. The inconsistency in the length of cardiac cycles can affect the LV filling and ejection times, which in turn can impact the assessment of LV function. Therefore, in AFib, it becomes crucial to select the appropriate cardiac cycle for evaluation.

A first cardiac cycle duration 336 is shown next to a second cardiac cycle duration 338 and a third cardiac cycle duration 340, and all three cardiac cycles have different durations. Additionally, in the ECG of the heart with AFib, there is no repeating pattern of cardiac cycle durations, meaning the durations of the cardiac cycles do not change with any regularity. Since AFib is caused by a non-functioning sinoatrial node, there is typically no visible P-wave in an AFib ECG. Instead of a regular cardiac cycle, an AFib ECG may contain F waves 342. F-waves are small, overlapping waves that represent the stimuli generated by the atria during fibrillation. F-waves may occur during the entire cardiac cycle, and may overlap the QRS complex and T wave. The F waves may typically have a low amplitude and may not impact the visibility of the QRS complex, but in some cases may mask the T wave. Cardiac cycles in an ECG of a patient with AFib may include an approximately normal QRS complex, such as a first QRS complex 330 or a second QRS complex 332. Cardiac cycles in an ECG of a patient with AFib may be defined based on the repetition of QRS complexes because other features of a cardiac cycle such as P-waves and T-waves may be missing or difficult to identify.

Based on an ECG, cardiac cycles visualized with the ECG may be identified as being suitable for use in downstream automatic measurements. For example, a first cardiac cycle 344 may be selected for use in analyzing the function of the patient's heart. The first cardiac cycle includes the first QRS complex 330, has a duration that is not significantly outside the average duration of heartbeats included within the second ECG graph 304, and includes a T wave 348. The T wave 348 is overlaid by F waves, and is not as clearly defined as the T waves visible in the ECG of a healthy heart (such as the first ECG graph 302). However, there is a positive deflection in the second ECG graph 304 following the first QRS complex 330. The first cardiac cycle 344 may therefore have enough characteristics of a regular cardiac cycle to be selected for analysis.

A second cardiac cycle 350 may be discarded and may not be used for analysis. The second cardiac cycle 350 has a duration that is significantly shorter than the average duration of the heartbeat which makes it ineligible for analysis. Additionally, the second cardiac cycle 350 lacks a visible T wave, which indicates that the second cardiac cycle 350 is not a normal cardiac cycle and heart function cannot be accurately assessed based on the second cardiac cycle 350. However, in many cases cardiac cycles measured by an ECG are not assessed on their suitability for downstream measurement. Selecting cycles for downstream measurement using an ECG is less ideal than selecting cycles based on the ultrasound videos because the ECG may lack the information necessary to identify cardiac subphases. In an ECG, features of the cardiac cycle may be identified based on the T-wave, P-wave and QRS complex. However, these features do not correspond exactly to the subphases of the cardiac cycle and it may be difficult to identify subphases such as isovolumetric relaxation (IVR) because the ECG lacks information about the motion of the mitral and aortic valves that are necessary to identify the subphases. Ultrasound videos may include images of the mitral and aortic valves that can be used to generate more precise subphase labels than are available using an ECG.

In addition, downstream measurements are often performed on ultrasound images and videos of the heart. In some examples, downstream measurements are performed automatically, and thus users may not be aware that unsuitable cycles are being used in the measurements. For example, ejection fraction is determined by determining the amount of blood retained within a heart versus the amount of blood ejected during the ejection subphase based on images of the left ventricle and the blood within the left ventricle at the end of systole and the end of diastole. When measuring ejection fraction without the ability to select suitable cycles, 10 cycles of an ultrasound video may be evaluated. The ejection fraction may be measured for each cycle from the ultrasound video of the heart. To determine the ejection fraction of the heart, the ejection fraction for each cycle may be measured and averaged. The 10 cycles may include cardiac cycles impacted by AFib, which includes cycles that are missing subphases of the cardiac cycle. In some examples, the ejection subphase may be interrupted by atrial fibrillation, which may significantly impact the measured ejection fraction of that cardiac cycle. Including cardiac cycles with impacted ejection fractions in the data set used to determine the average ejection fraction may skew the average ejection fraction. Similarly, myocardial strain may be determined by determining the myocardial strain of each cardiac cycle based on measurements from an ultrasound of the heart and averaging all of the myocardial strain measurements. The average myocardial strain may also be impacted by the inclusion of cardiac cycles impacted by AFib. Including cycles impacted by AFib means that cardiac cycles that do not include all phases of a cardiac cycle may be averaged among complete cardiac cycles, which may skew any downstream measurements performed using the average values. When available, an ECG of the heart synched to the ultrasound video may be used to select cycles suitable for left ventricle function. However, ECG typically does not visualize the transition from rapid inflow to diastasis and thus does not provide a precise mechanism to determine the cycles most suitable for evaluation of left ventricle function. Further, ECG demands placement of electrodes on the patient, synchronization with the ultrasound video, and proper interpretation, each of which may limit usage of ECG during ultrasound acquisition.

The embodiments disclosed herein allow for automatic selection of one or more cardiac cycles suitable for performing downstream automatic measurements, such as metrics of left ventricle function like ejection fraction and cardiac strain. The method described herein is capable of automatically separating a video of a beating heart into distinct cardiac cycles with one or more subphases labelled and then determining if each cardiac cycle is suitable for use in automatic measurement, using only the medical image frames of the video to determine cycle suitability and not ECG data. The method described herein uses a timing model such as timing model 208 model trained on labelled ultrasound videos of beating hearts imaged from three different planes of view. Events such as the opening and closure of valves within the heart may be captured on the video of the beating heart. Using this data to train the timing model allows for the model to learn what features in the medical image frames of a 2-D ultrasound video correspond to each subphase of the cardiac cycle. Based on the presence and duration of subphases of the cardiac cycle in one cycle in a 2-D video, the cycle can either be labelled suitable or unsuitable for use in automatic measurement without the use of an ECG. Medical image frames from suitable cycles can be saved and medical image frames from unsuitable cycles can be deleted. Only saving suitable cycles may reduce the memory demand on the system compared to the memory use of a system that involves obtaining medical image frames over a relatively large number of cardiac cycles (e.g., 10), performing the measurement (e.g., of strain or ejection fraction) for each of the cardiac cycles, and then averaging the measurements.

Benefits of the above method further include increased accuracy in identifying the start and end of phases of a cardiac cycle compared with identifying the phases of a cardiac cycle from an ECG. There may be significant advantages to automatically identifying the start and end times of phases of the cardiac cycle from a video compared to identifying the duration of phases from an ECG. For example, many downstream measurements such as ejection fraction and myocardial strain involve comparing the state of the heart between end diastole (ED) and end systole(ES). ED on an ECG is typically identified as the R-peak of the QRS complex. However, the ECG represents electrical signals in the heart, and the R-peak typically precedes the end of LV filling by a duration of time. ED and ES can be determined more accurately through an ultrasound video by timing the closure of the mitral and aortic valves. More accurate timing of ED and ES allows measurements such as ejection fraction and myocardial strain to be taken using medical image frames of the ultrasound that more precisely match ED and ES, which may increase accuracy in the measurement of ejection fraction and myocardial strain. Additionally, there are currently no established guidelines for determining the timing of the mitral and aortic valve openings (MVO, AVO) from an ECG. In some LV function assessments, it may be necessary to determine the timing of MVO and AVO, which may be accomplished by analyzing an ultrasound video. However, it may be difficult for a human to accurately assess the timing of MVO and AVO based on medical image frames of an ultrasound video due to challenges such as poor image quality. More accurate timing may be achieved by the timing model 208.

Additionally, not using an ECG may save time, as a clinician does not have to place the electrodes necessary to perform an ECG on the precise locations on the body of the patient.

Turning now to FIG. 4, it shows a flow chart illustrating an example method 400 for obtaining and analyzing a 2D video of a patient's heart to perform measurements on only the frames of the 2D video that depict cardiac cycles that are suitable for use in an automatic measurement, and not on the frames of the 2D video that depict cardiac cycles that are not suitable for use in the automatic measurement. Method 400 is described with regard to the systems and components of FIGS. 1-2, though it should be appreciated that the method 400 may be implemented with other systems and components without departing from the scope of the present disclosure. Method 400 may be carried out according to instructions stored in non-transitory memory of a computing device, such as memory 120 of FIG. 1 or memory 206 of FIG. 2, and executed by a processor of the computing device, such as processor 116 of FIG. 1 or processor 204 of FIG. 2.

At 402, method 400 includes obtaining an apical 2D video of the patient's heart. An apical 2D video of the heart is a video that images the heart along the coronal plane of the heart. The apical view may include a view of all four chambers of the heart (a 4CH view), two chambers of the heart (a 2CH view), or an apical long axis view (APLAX). An ultrasound imaging system such as the ultrasound imaging system 100 may be used to obtain the apical 2D video. At 404, the method may include entering medical image frames of the 2D video as input to a timing model, such as the timing model 208 included in the image processing system 202. In some examples, the timing model may receive a real time, or near real time, 2D apical video feed of the heart. Real time may refer to a process that occurs simultaneously with of the collection of the 2D apical video feed of the heart. Near real time may refer to a process that is delayed from real time by a processing time, such as the time it takes for the timing model to be applied to the video feed of the heart. In another example, an apical 2D video of the patient's heart including multiple cardiac cycles may be input to the timing model at some point in time after the video was collected from the patient. The 2D video may be stored temporarily in memory such as a buffer or other temporary memory while the video is analyzed.

In some examples, the medical image frames of the 2D video are automatically entered into the timing model when the medical image frames are acquired. For example, the 2D video may be acquired according to a scan protocol that dictates the one or more measurements be performed, and the image processing system may automatically enter the medical image frames as input to the timing model based on the scan protocol. In another example, the medical image frames of the 2D video may be input to the timing model responsive to a user command to analyze the video or perform a measurement on the video, through a user input device such as user input device 232.

The timing model may generate output usable to assign each frame in each cardiac cycle of the video to a subphase of the cardiac cycle based on the characteristics of the frame and the position of the frame among other medical image frames in the 2D video. The timing model may include a convolutional neural network (CNN) layer and a recurrent neural network (RNN) such as one or more LSTM layers that may be trained to identify cardiac cycle events based on spatial and temporal information in the frames (e.g., spatial information in a given frame and temporal information of the given frame relative to neighboring frames). In some examples, the frames may be entered to the timing model in sets/blocks of frames. Additional information about the timing model, including how the timing model is trained, are provided below with respect to FIGS. 7-10.

At 406, the output of the timing model is received. The output may include the medical image frames of the apical 2D video that were input to the timing model, with each output frame labeled by cardiac cycle subphase. In other examples, the labels may only include labels for the first frame of each subphase. In some examples, the timing model may output a plurality of prediction curves, with each prediction curve corresponding to a subphase. Each prediction curve provides a probability, for each frame, that the frame depicts that subphase. The labels may be determined from the prediction curves, as explained in more detail below with respect to FIGS. 7-10. A pictorial representation of the output of the timing model is shown in FIG. 6 and described in more detail below.

At 408, the method 400 may include determining the suitability for each cycle to be used in automatic measurements of left ventricle function, such as ejection fraction, AFI, etc., based on the output from the timing model. The suitability for each cycle may be determined according to decision logic described in more detail with respect to FIG. 5. The suitability of a cardiac cycle may depend on the length of the cardiac cycle compared to other cardiac cycles, the presence of one or more subphases of the cardiac cycle, the length of diastole relative to the length of systole, and/or combinations thereof.

At 410, the method 400 may include saving the medical image frames that comprise the cardiac cycle or cycles determined to be suitable at 408. The medical image frames of the cycle(s) determined to be suitable may be saved in permanent memory, such as memory 206 (e.g., as part of ultrasound image data 210). In some examples, the medical image frames of the cycle(s) determined to be suitable may be included as part of an exam/report for the patient and thus also eventually saved in an image archive such as a picture archive and communication system. The medical image frames of cardiac cycles determined to be unsuitable may be deleted (or otherwise not saved to permanent memory) in order to reduce the amount of memory demanded for performing the measurement. In the example that an approximately real time video is submitted to the timing model, medical image frames may be saved or deleted in approximately real time (e.g., once a complete cardiac cycle is captured and accounting for a delay as the medical image frames are analyzed). [Once a predetermined amount of medical image frames of suitable cycles has been saved (e.g., three cycles), a message may be conveyed to a clinician via a display device like display device 234 to indicate that the clinician no longer needs to continue imaging the patient for the purposes of collecting video for performing the measurement. In the example that a video is analyzed after it has been collected from the patient, the medical image frames corresponding to the suitable cycles may be presented to the user (e.g., a clinician performing the ultrasound or reviewing the results of the ultrasound at a later time) and the user may confirm that the selected cycles are suitable. If the user disagrees with the selection of the cycles, the user may override the selected cycles and choose other cycles from the video for analysis, obtain another video (if possible), or indicate that the measurement should be performed across a larger number of cycles (e.g., 10) and then averaged.

At 412, the method 400 may include performing one or more measurements on the saved medical image frames. These measurements may include the ejection fraction, AFI, and/or other measurements that evaluate the function of the left ventricle. The one or more measurements may be performed (e.g., by the image processing system) automatically or in response to a user request to perform the one or more measurements. In the example that no suitable medical image frames were saved at 410, measurements cannot be performed and an error may be displayed via a display device such as display device 234 that may prompt clinicians to continue collecting video of the patient's heart.

FIG. 5 is a flowchart that illustrates an example method 500 that includes decision logic for identifying suitable cardiac cycles for automated measurement from a 2D video of a patient's heart wherein each frame has been labelled to identify the subphase of the cardiac cycle captured in that frame. Method 500 is described with regard to the systems and components of FIGS. 1-2, though it should be appreciated that the method 500 may be implemented with other systems and components without departing from the scope of the present disclosure. Method 500 may be carried out according to instructions stored in non-transitory memory of a computing device, such as memory 120 of FIG. 1 or memory 206 of FIG. 2, and executed by a processor of the computing device, such as processor 116 of FIG. 1 or processor 204 of FIG. 2.

At 502, the method 500 includes obtaining a 2D video of the patient's heart and the output from a timing model, such as timing model 208. The output of the timing model includes a label for each frame that identifies the subphase the frame belongs to and, in some examples, a time indicator associated with each frame. The method 500 may be performed without the use of an ECG signal of the patient. However, measurements from an ECG may be used to confirm or measure the duration of each cardiac cycle within the 2D video, which may increase the confidence of the determination of the cardiac cycle length. As explained above, the subphases may include atrial systole, diastasis, rapid inflow, IVR, ejection, and IVC.

At 503, the method 500 includes segmenting the video into cardiac cycles. In one example, a cardiac cycle may be defined as the medical image frames of the video between a first MVC event and a subsequent MVC event. However, the cardiac cycle repeats and thus may be defined as the frames of the video between two of the same cardiac event. For example, a cardiac cycle could be defined as the frames between two subsequent MVO events or AVO events. As the medical image frames are captured and processed through the timing model, the frames that include the events described above may be labeled. Once a complete cardiac cycle is identified (e.g., once two of the same type of cardiac event have been identified), the frames of the complete cardiac cycle may be evaluated with the decision logic as described below.

At 504, the method 500 includes evaluating a selected cycle. In some examples, evaluation of a selected cycle may commence once all medical image frames of the selected cycle have been labeled via the timing model. In some examples, the evaluation of the selected cycle may commence once medical image frames of additional cycles the video have been labeled via the timing model.

Evaluating the selected cycle may include determining if one or more subphases are missing at 506. A missing subphase may indicate that the cycle was impacted by a condition such as AFib and is unsuitable for automated measurement. A subphase may be determined to be missing if no medical image frames are labeled as depicting that subphase in the selected cardiac cycle. In some examples, only one or more selected subphases may be evaluated at 506. For example, atrial systole is frequently absent in cardiac cycles impacted by AFib, so in some examples the selected cycle may be determined to be missing a subphase only if atrial systole is missing, and the selected cycle may not be evaluated based on the presence or absence of all other cardiac cycle subphases. In other examples, the selected cycle may be determined to be missing a subphase if any of the subphases are missing. If a subphase is missing (e.g., if atrial systole is missing), the method may proceed to 512, which may include indicating the selected cycle is unsuitable. Indicating the selected cycle is unsuitable may provide information used in the method 400 at 410 to determine if the cycle is saved or deleted.

If no subphases are missing at 506 (e.g., all subphases are imaged for the selected cardiac cycle), the method 500 may optionally include determining if the duration of diastole is outside a threshold range relative to the duration of systole at 508. Diastole is the phase during which the heart muscles are relaxed and the chambers fill with blood and may be comprised of the period of time between AVC and MVC and thus may include the IVR, rapid inflow, diastasis, and atrial systole subphases. Using the labelled and timestamped medical image frames output by the timing model, the time between AVC and MVC including AVC, MVO, DSS, and ASS can be calculated and the duration of that period may be referred to as the duration of diastole. In other examples, the medical image frames may not be time-stamped, and the duration of diastole may be determined from the number of medical image frames labeled as IVR, rapid inflow, diastasis, and atrial systole. Systole is the phase during which the heart muscles contract and the blood in the heart is pumped through the body. Systole may be comprised of the subphases between MVC and AVC and thus may include the ejection and IVC subphases and the duration of that period (determined based on the time between the first frame labeled as ejection and the final frame labeled as IVC, or based on the total number of medical image frames labeled as ejection and IVC) may be referred to as the duration of systole. In a normal heart, diastole is longer than systole. However, systole may begin before diastole is over in a heart experiencing AFib, which may make diastole shorter than systole. Thus, the decision logic may include determining if diastole length is outside a threshold range of systole length. For example, being outside the threshold range may include diastole being shorter than 0.8× systole or 1.2× systole. If diastole duration is out of range, the method may include indicating the cardiac cycle is unsuitable at 512.

If diastole duration is not out of range (e.g., if diastole is not shorter than systole) at 508, the method may include, at 510, determining if the cardiac cycle duration is too short. An average cycle duration may be calculated cumulatively based on the cycles that have been analyzed prior to the selected cycle or the average cycle duration may be determined over all cycles of the video. In one example, if the duration of the selected cycle is less than 75% of the average cycle duration, the selected cycle may be too short and may be indicated as unsuitable at 512. In another example, if the duration of the selected cycle is more than one standard deviation away from the average cycle duration, the selected cycle may be indicated as unsuitable at 512. If the cycle is not too short at 510, the method may proceed to 514, where the method 500 may include indicating that the cycle is suitable. Indicating a cycle is suitable may provide information used in the method 400 at 410 to determine if the cycle is saved or deleted.

In some examples, the decision logic may only include evaluation of missing subphases and/or evaluation of the length of diastole and may not evaluate the length of the selected cycle relative to the average cycle length. In such examples, once the selected cycle is determined to be suitable at 506 or at 508, method 500 may proceed to 516 without evaluating cycle length. In other examples, the cycle length may be evaluated at 510 after a threshold number of cycles have been recorded (e.g., five cycles, ten cycles) and labeled via the timing model. Some metrics, such as the short cycle length metric evaluated at 510, may demand multiple cycles, so having additional metrics to evaluate adds more information and allows more accurate determination of suitable cycles. But, using subphases to do the prediction only demands one complete cycle and can be done in real time or approximate real time. The presence of all subphases or at least selected subphases (at 506) or relative length of phases (at 508) do not utilize more than one cycle and thus the determination of whether the selected cycle is suitable may be performed more rapidly based on these metrics. As an example, it would also be possible to exclude the short cycle length metric at the start of a recording of the heart (either started explicitly by the user, or by analyzing the video continuously in the background), and then include the short cycle length in the evaluation when/if more cycles are recorded.

At 516, the method 500 may include determining if there are more cycles to be evaluated. If there is at least one cycle within the video that has not been evaluated for suitability, the method 500 may include selecting one of the cycles that has not been evaluated and evaluating that cycle at 504. If all the cycles of the video have been evaluated for suitability, the method may end. In some examples, once a predetermined number of cycles have been evaluated and determined to be suitable (e.g., three cycles), the method may end even if more cycles of the video have yet to be analyzed.

FIG. 6 is a visualization of the output of a timing model applied to a 2D APLAX recording from a normal patient. A still frame 602 of the 2D APLAX recording of the normal patient is shown for reference. A plot 604 includes a visual representation of the output of the timing model. The plot includes a horizontal axis 606 that represents the passage of time and a vertical axis 608 upon which the labels of the cardiac cycle are labeled. The plot 604 is made up of a plurality of dots located at a specific horizontal and vertical position. Each dot represents a frame of the 2D APLAX recording, where the horizontal position signifies the time the frame was recorded and the vertical position represents which subphase of the cardiac cycle the frame was determined to belong in by the timing model. Along the horizontal axis 606, vertical dashed lines are marked and labeled with an abbreviation of an event used by the timing model to signal the start of a subphase. For example:

MVC: First frame where the mitral valve was closed.

AVO: First frame where the aortic valve was open.

AVC: First frame where the aortic valve was closed.

MVO: First frame where the mitral valve was open.

DSS: First frame where the anterior mitral leaflet stopped its movement towards the left atrium after opening.

ASS: First frame where the anterior mitral leaflet moved towards the LV after diastasis.

Each labelled dashed line indicates the frame at which the labelled event occurred (referred to as an event frame). Each frame between an event frame and the frame chronologically before the next event frame may be assigned to the same subphase by the timing model. Medical image frames sharing the same subphase have the same vertical position on the plot 604.

The medical image frames between AVC and MVO belong to the isovolumetric relaxation (IVR) subphase. The medical image frames between MVO and DSS belong to the rapid inflow subphase. The medical image frames between DSS and ASS belong to the diastasis subphase. The medical image frames between ASS and MVC belong to the atrial systole subphase. The medical image frames between AVC and MVC belong to the systole phase 610. The medical image frames between MVC and AVO belong to the isovolumetric contraction (IVC) subphase. The medical image frames between AVO and MVC belong to the ejection subphase. The medical image frames between MVC and AVC belong to the diastole phase 612. In some examples, the plot shown in FIG. 6 may be displayed on a display device such as display device 118 so that a user can see the model output. In some examples, a user may monitor the output (e.g., labeled frames) for aberrations and may be able to confirm or override the selection of cycles. For example, a user may be able to manually remove a cycle that they do not wish to include in further analysis.

FIG. 7 is a flow chart illustrating an example method 700 for training a timing model, such as timing model 208. Method 700 is described with regard to the systems and components of FIGS. 1-2, though it should be appreciated that the method 700 may be implemented with other systems and components without departing from the scope of the present disclosure. Method 700 may be carried out according to instructions stored in non-transitory memory of a computing device, such as memory 206 of FIG. 2 (e.g., in training module 212), and executed by a processor of the computing device, such as processor 204 of FIG. 2.

At 702, method 700 includes obtaining labeled triplane videos of the heart of a plurality of patients. Each labeled triplane video may include a sequence of triplane ultrasound images obtained with a 3D probe, with each triplane image including three simultaneously-captured orthogonal views of the heart, such as three orthogonal apical views (e.g., 2-chamber (2CH), 4-chamber (4CH), and apical long axis (APLAX)). Each triplane image that signals/includes an event of the cardiac cycle that marks a new subphase may be labeled as such (e.g., AVO, MVO, AVC, MVC, ASS, and DSS), as determined by an expert(s) viewing the triplane images. By using the triplane images, the cardiac cycle events that are only visible in one or two of the views may be used to label all the views. For example, an aortic valve event (e.g., AVO, AVC) may only be visible in an APLAX view, but the 2CH and 4CH views obtained at the same time as the APLAX view may likewise be labeled with the aortic valve event, allowing the timing model to learn features in the 2CH and 4CH views indicative of aortic valve events.

At 704, each triplane video is split into labeled, single-view videos that each include a sequence of medical image frames from the triplane video showing only a single view from the triplane video, in order to form training data to be used to train the timing model. For example, a labeled triplane video may be split into a first single-view video including medical image frames of only the 2CH views of the labeled triplane video, a second single-view video including medical image frames of only the 4CH views of the labeled triplane video, and a third single-view video including medical image frames of only the APLAX views of the labeled triplane video. Each single-view video may include the same labels as the triplane video, so that each view of a labeled triplane image includes the label associated with that triplane image. For example, a given triplane image of the triplane video may be labeled DSS due to one or more views of the triplane image showing the anterior mitral leaflet stopping its movement toward the left atrium after opening. When the triplane video is split into the separate single-view videos, each frame originating from the given triplane image may be labeled DSS as well.

It is to be appreciated that not all triplane images, and thus not all medical image frames of each single-view video, may be labeled by the expert(s), as the events described herein include only the first frame where the event is visible. The medical image frames of each single-view video are maintained in temporal order, such that medical image frames between a frame labeled AVO and a subsequent frame labeled AVC may be assumed to be medical image frames that capture the ejection subphase, the medical image frames between the frame labeled AVC and a subsequent frame labeled MVO may be assumed to be medical image frames that capture the IVR subphase, etc. Thus, in some examples (such as when the initial timing model is a classification network, explained in more detail below), each frame may be labeled by subphase as explained above (e.g., the frame labeled AVO and the medical image frames thereafter, but before the subsequent frame labeled AVC, may be labeled as the ejection subphase). In other examples (such as when the initial timing model is a regression network, as explained below), each expert-labeled frame is labeled as indicated by the expert(s) and neighboring medical image frames are labeled with the same label but with lower weights further from the expert-labeled frame. For example, an expert-labeled frame may be given a weight of 1, with weights reduced linearly to 0 at a 5-frame distance from the expert-labeled frame. In such examples, some medical image frames may include multiple labels.

At 706, a sequence of medical image frames from a selected labeled single-view video is entered as input to an initial timing model. The sequence of medical image frames may include a fixed number of medical image frames (e.g., 30 medical image frames) or a random number of medical image frames and each of the selected labeled single-view video and the sequence from the selected labeled single-view video may be selected from the training data randomly. The initial timing model may be an untrained, or partially trained, version of the timing model. The initial timing model may be a classification network or a regression network. Both the classification network and the regression network use a combination of convolutional layers to detect spatial image features followed by long short-term memory (LSTM) layers to account for the temporal changes from image to image.

When the initial timing model is a classification network, the initial timing model may include a CNN layer (e.g., five blocks of 3D convolution layers), two LSTM layers, and an output layer (e.g., a ID convolution layer). When the initial timing model is a regression network, the initial timing model may include a pre-trained CNN (e.g., pre-trained on an image dataset, such as an ImageNet dataset), two LSTM layers, and an output layer (e.g., a dense network with sigmoid activation). Thus, in either example, the sequence of medical image frames is input to a CNN layer of the initial timing model. In some examples, three medical image frames of the sequence may input together to the initial timing model, and a training round may be completed once all medical image frames of the sequence have been entered as input to the initial timing model. One output of the initial training model may be produced for each sequence of medical image frames that is input to the model, as explained below. In this way, three medical image frames of the sequence may be entered as input at a time, but the initial timing model may not produce an output until all medical image frames of the sequence have been input and processed via the initial timing model.

At 708, method 700 includes receiving predictions output by the initial timing model. The predictions may include a predicted subphase for each input frame (in the case of the classification network) or a predicted event for each input frame including a confidence/weight (in the case of the regression network). In either case, the output from the initial timing model may include a prediction curve for each subphase. The subphase and/or event for each frame of the sequence is derived based on the predictions, as indicated at 710. For example, when the initial timing model is the classification network that outputs a prediction of a subphase for each frame, the subphases may be determined directly from the predictions and the events derived based on the subphase predictions across medical image frames of the sequence by finding the transitions from one subphase to the next. When the initial timing model is the regression network that outputs a weighted prediction of an event for each frame, the events are derived from the predictions by finding the peak of each event label (e.g., of each prediction curve).

At 712, a loss function is calculated based on the derived/predicted subphase and/or event for each frame (as determined based on the output of the initial timing model) and the actual label (e.g., the ground truth) for each frame of the sequence. In some examples, the loss function may be calculated once multiple sequences have been input to the initial training model (e.g., the loss function may be calculated after a batch of sequences has been input to the model and processed to produce a batch of outputs). The loss function may be categorical cross entropy (for the classification network) or mean square error (for the regression network), for example. The loss function is used to update the initial model, as indicated at 714. For example, via backpropagation, the weights of the initial timing model may be updated in order to minimize the loss function.

At 716, the above process is repeated until the initial timing model is trained. For example, a new batch of sequences may be selected as described above, entered as input to the initial timing model, and the initial timing model updated based on the loss function calculated from the predictions output by the initial timing model. An epoch of training may be completed once each frame of the training data has been entered as input, and a plurality of epochs may be performed to fully train the timing model (e.g., 100 epochs, 200 epochs). At 718, the trained timing model may be validated. For example, a portion of the initial training data may be set aside as test data and used to validate (e.g., test) the trained model. In some examples, 10-fold validation may be performed such that each frame of the training data may be used to both train the timing model and test the timing model. The final version of the timing model that is deployed as described herein may be an ensemble average of the 10 trained models (e.g., where each model is trained on one set of the training data, and 10 sets of the training data are used for the 10-fold training and validation). Method 700 then ends.

FIG. 8 schematically shows an example process 800 for training a timing model, such as timing model 208. Process 800 may be a schematic illustration of method 700. As explained above, the initial timing model may be trained to become the trained timing model using a plurality of triplane videos. Each triplane video may include a plurality of triplane images, such as triplane image 802. As shown in FIG. 8, the triplane image 802 includes three apical views (4CH, 2CH, and APLAX) captured simultaneously or nearly-simultaneously. In one non-limiting example, the triplane videos may be captured with a frame rate of 48 fps, with the triplane images acquired by alternating between each plane/view for a total of 144 image planes/views per second (e.g., such that the three views of a given triplane image are obtained within 0.02 seconds of each other). During the annotation process, the three views of each triplane image are viewed by the annotator at the same time. However, it is to be appreciated that the actual triplane image data may include a separate image for each triplane view (e.g., such that a 2CH image, a 4CH image, and an APLAX image are collected as a triplane image and displayed on a display screen at the same time for annotation). The expert(s)/annotator(s) may label each triplane image that includes an event that meets the conditions described above (e.g., MVC is the first frame where the mitral valve is closed, AVO is the first frame where the aortic valve is open, etc.).

The result is a labeled triplane video 804, wherein triplane images of the triplane video that include an event are labeled as such; intervening triplane images may not be expert-labeled.

The labeled triplane videos are then split into single-view videos. For example, the labeled triplane video 804 may be split into a first single-view video 806 (e.g., a 4CH video including only the 4CH images/frames of the labeled triplane video 804), a second single-view video 808 (e.g., a 2CH video including only the 2CH images/frames of the labeled triplane video 804), and a third single-view video 813 (e.g., an APLAX video including only the APLAX images/frames of the labeled triplane video 804). Each of the single-view videos may include labels on the frames originating from a labeled triplane image. For example, in the labeled triplane video 804, a first labeled triplane image may be labeled MVC by an expert. The first labeled triplane image is split so that each view/plane of the first labeled triplane image is included in a respective single-view video, and those frames may each be labeled as MVC (such that each single-view video includes a first labeled frame that is labeled as MVC).

The above process is performed for each of a plurality of triplane videos to form training data 810. In the example shown, the training data 810 may include labeled, single-view videos from 240 triplane videos (e.g., each of a different patient), though other amounts of training data are possible. Further, while not shown in FIG. 8, it is to be appreciated that the single-view videos of training data 810 may include one or more labels for each frame, as discussed above with respect to FIG. 7 (e.g., frames may be labeled by subphase or weighted event depending on temporal relation to labeled event frames). To train the initial timing model, a sequence of frames is randomly selected from training data 810, such as sequence 811. The sequence 811 may be a subset of frames (e.g., 30 frames) from the first single-view video 806 in the example shown in FIG. 8.

Each frame of the sequence 811 is then entered as input to the initial timing model. As shown, a set of frames 812 (e.g., three frames) is entered as input to an initial timing model 814. In some examples, the set of frames 812 may include a first frame and one or more frames adjacent to the first frame in time. For example, the first frame, the frame before the first frame, and the frame after the first frame may all be input together into the initial timing model 814. In this way, the set of frames 812 forms a three dimensional block of the frame width by the frame height by three frames. As explained previously, the initial timing model 814 (and the fully trained timing model once training is complete) includes a CNN layer and two LSTM layers. The frames within the set of frames 812 may each be run through the CNN and the LSTM layers. The LSTM layers may be bidirectional or forward-only. For example, the output from the CNN and the output from one or more neighboring LSTMs may be used as input for a first LSTM layer. The CNN is the same for all frames (once trained) and the same image input would be expected to return the same output at any time, as the CNN is only concerned with the spatial information of the frame (with the exception that some temporal information is included here as well by combining three frames in a 3D block). The LSTM is different in that it includes as input both the output from the CNN, and the output from neighboring LSTMs (bidirectional in the example shown in FIG. 8, but the LSTMs could also be forward-only for real time application). In this way, the LSTM may take into account more temporal information, which is advantageous in predicting subphase because the evaluation of the subphase of one frame can only be evaluated in the context of the sequence of frames. So, the input includes a set of frames (three is illustrated in FIG. 8, but the set of frames could include one or more frames) to the timing model at the initial CNN stage, but the timing model also takes as input (intermediate) results from other frames in the sequence.

For example, for a current set of frames, the output from the CNN layer (generated based on the current set of frames), the output from the first LSTM layer corresponding to a prior set of frames (e.g., the output from the first LSTM layer in a prior iteration before the current set of frames), and the output from the first LSTM layer corresponding to a subsequent set of frames (e.g., the output from the first LSTM layer in a subsequent iteration after the current set of frames) may be used as input for the first LSTM layer. When the LSTM is a forward-only, the output from the CNN layer and the output from the first LSTM layer corresponding to the prior set of frames may be used as input for the first LSTM layer. Similarly, the second LSTM layer may be bidirectional or forward-only. The bidirectional configuration may result in more temporal information being taken into account when classifying the frames, but may be more time consuming and consume more processing resources than the forward-only configuration. In some examples, a different kind of recurrent neural network (RNN) may be used in place of an LSTM, such as a gated recurrent unit (GRU).

The initial timing model 814 may output a set of prediction curves 816. The set of prediction curves 816 may include a curve for each subphase for each input frame (in the case of the classification network) or a curve for each event for each input frame. Based on the set of prediction curves 816, a subphase may be assigned to each frame of the sequence 811 and an event may be assigned to each frame of the sequence 811 that is determined to include an event. Additional details about the prediction curves are provided below with respect to FIGS. 9 and 10. A loss function is then calculated based on the assigned subphases/events relative to the labeled subphases/events of the sequence 811, and the initial timing model 814 is updated (e.g., via backpropagation) based on the loss function.

Once the model is trained, inference may be performed on a video of a patient that captures an apical view of the heart (e.g., 2CH, 4CH, or APLAX). For example, a 4CH video 818 of a patient may be entered as input to the trained timing model, and the timing model may generate output 820 that includes assigning a respective event to the frames that meet the conditions set forth above, with the intervening frames being assigned to the appropriate subphase, as explained above. For example, a frame labeled MVC may be assigned to the IVC subphase, and all frames thereafter but before a subsequent framed labeled AVO may also be assigned to the IVC subphase. The frame labeled AVO may be assigned to the ejection subphase, and all frames thereafter but before a subsequent frame labeled AVC may be assigned to the ejection subphase as well. In some examples, the labelled frames may be reviewed by a clinician to confirm the timing of the subphases of the cardiac cycle. In the example that the clinician disagrees with the labelled frames, it may be possible for the clinician to relabel the frames before the frames are used to determine the suitability of the cardiac cycle for use in the assessment of LV function. In other examples, the relabeled frames may be incorporated into the training data of the timing model to increase the accuracy of the timing model.

FIG. 9 shows a first example set of plots 900 that shows frame labels and prediction curves that may be used by and output by, respectively, a timing model during training, when the timing model is a classification network. The first example set of plots 900 includes a first plot 902 showing frame labels for a sequence of frames that may be used during training and a second plot 920 showing prediction curves for the sequence of frames as output by the timing model. For the classification network, each frame of the training data is labeled by its subphase. Thus, the first plot 902 includes a label curve for each subphase that shows a probability (on a scale of 0 to 1, plotted on the y axis) of each frame of the sequence (plotted along the x axis) belonging to that subphase. The label curves may include an atrial systole curve 904, a diastasis curve 906, a rapid inflow curve 908, an IVR curve 910, an ejection curve 912, and an IVC curve 914. Because the first plot 902 is showing labels that are assigned based on expert feedback, each frame has a probability of 0 or 1. The first plot 902 further includes event timings (e.g., showing MVC, AVO, AVC, MVO, DSS, and ASS). Each event timing represents the first frame of the corresponding subphase.

The second plot 920 likewise includes a label curve for each subphase, as output from the timing model, including an atrial systole curve 924, a diastasis curve 926, a rapid inflow curve 928, an IVR curve 930, an ejection curve 932, and an IVC curve 934. The timing model may output a respective probability, for each frame of the sequence, that the frame belongs to each subphase. As such, while the majority of frames include a probability of 0 for all subphases other than one subphase (which is given a probability of 1), some frames may be given a probability above 0 for more than one subphase (e.g., the frames at the end of the ejection subphase may be labeled as both ejection and IVR, with ejection having a higher probability). The events are derived from the subphase predictions by finding the transitions from one phase to the next. For example, AVO may be derived as the frame where IVC and ejection have the same probability (with frames before having a higher probability of IVC and frames thereafter having a higher probability of ejection).

FIG. 10 shows a second example set of plots 1000 that shows frame labels and prediction curves that may be used by and output by, respectively, a timing model during training, when the timing model is a regression network. The second example set of plots 1000 includes a first plot 1002 showing frame labels for a sequence of frames that may be used during training and a second plot 1020 showing prediction curves for the sequence of frames as output by the timing model. For the regression network, each frame is labeled by event, or by proximity to a nearby labeled event. Thus, the first plot 1002 includes a label curve for each event that shows a probability (on a scale of 0 to 1, plotted on the y axis) of each frame of the sequence (plotted along the x axis) belonging to that event. The expert may label the frames showing the events according to the criteria set forth above, and neighboring frames may be labeled with the same event but with progressively lower weight/probability. Thus, the label curves may include an MVC curve 1004, an ASS curve 1006, a DSS curve 1008, an MVO curve 1010, an AVC curve 1012, and an AVO curve 1014. The peak of each curve corresponds to the frame given that event label by an expert, and each curve decreases linearly from the peak, on either side, due to the linearly decreasing probability, until a probability of 0 is reached (e.g., the probability may decrease linearly until 0 for five frames on either side of the peak).

The second plot 1020 likewise includes a label curve for each event, as output from the timing model, including an MVC curve 1024, an ASS curve 1026, a DSS curve 1028, an MVO curve 1030, an AVC curve 1032, and an AVO curve 1034. The timing model may output a respective probability, for each frame of the sequence, that the frame belongs to each event. The events are derived from the predictions by finding the peak of each prediction curve. For example, AVO may be derived as the frame where the AVO curve reaches a peak. In some examples, a smoothing algorithm such as a weighted or unweighted rolling average may be applied to the curves to identify a peak. In other examples, non-linear interpolation techniques may be applied to determine the nearest frame to a peak when a cardiac event occurs between frames. In another example, the timing model may be configured to process multiple (e.g., two or more) overlapping sequences of frames to output multiple timing predictions for each frame. The predictions may then be averaged to determine a final timing prediction with greater accuracy.

A technical effect of using a timing model to identify the subphases of the cardiac cycle present in an ultrasound video is that cardiac cycles that are unsuitable for use in downstream measurement due to missing subphases of the cardiac cycle or other parameters indicative of a shortened/unrepresentative cardiac cycle can be identified and discarded automatically, thereby reducing errors in downstream measurements that use the video of the heart during specific subphases of the cardiac cycle. In doing so, the accuracy of measurements such as myocardial strain and ejection fraction can be increased, and fewer computing resources may be used by only performing analysis on image frames that depict cardiac cycles that are determined to be complete and representative of full left ventricle function.

The disclosure also provides support for a method, comprising: obtaining a sequence of medical image frames of a heart of a patient over a plurality of cardiac cycles, each medical image frame in the sequence depicting a same apical view of the heart, determining, based on output from a timing model trained to generate output usable to label each frame of the sequence by cardiac cycle subphase, a suitability of each cardiac cycle for performing an automated measurement, determining, based on the suitability of each cardiac cycle, that a first cardiac cycle is not suitable, and in response, not performing the automated measurement on medical image frames of the sequence that correspond to the first cardiac cycle, and determining, based on the suitability of each cardiac cycle, that a second cardiac cycle is suitable, and in response, performing the automated measurement on medical image frames of the sequence that correspond to the second cardiac cycle. In a first example of the method, determining, based on output from the timing model trained to generate output usable to label each frame of the sequence by cardiac cycle subphase, the suitability of each cardiac cycle for performing the automated measurement comprises: entering the sequence of medical image frames as input to the timing model, receiving the output from the timing model, and assigning a respective cardiac cycle subphase to each medical image frame of the sequence based on the output, wherein each respective cardiac cycle subphase is selected from a plurality of cardiac cycle subphases. In a second example of the method, optionally including the first example, the output comprises a plurality of prediction curves, each prediction curve corresponding to a respective subphase of the plurality of cardiac cycle subphases and including a probability of each medical image frame of the sequence belonging to that cardiac cycle subphase, and wherein assigning the respective cardiac cycle subphase to each medical image frame of the sequence based on the output comprises assigning the respective cardiac cycle subphase to each medical image frame of the sequence based on the plurality of prediction curves. In a third example of the method, optionally including one or both of the first and second examples, the output comprises a plurality of prediction curves, each prediction curve corresponding to a respective event of a plurality of events and including a probability of each medical image frame of the sequence belonging to that event, and wherein assigning the respective cardiac cycle subphase to each medical image frame of the sequence based on the output comprises assigning the respective cardiac cycle subphase to each medical image frame of the sequence based on the plurality of prediction curves. In a fourth example of the method, optionally including one or more or each of the first through third examples, each event of the plurality of events signals a transition to a new cardiac cycle subphase, and wherein assigning the respective cardiac cycle subphase to each medical image frame of the sequence based on the plurality of prediction curves comprises identifying which medical image frames of the sequence correspond to each event by identifying peaks in the plurality of prediction curves, and assigning the respective cardiac cycle subphase to each medical image frame of the sequence based on proximity to the medical image frames of the sequence that correspond to each event. In a fifth example of the method, optionally including one or more or each of the first through fourth examples, determining, based on output from the timing model trained to generate output usable to label each frame of the sequence by cardiac cycle subphase, the suitability of each cardiac cycle for performing the automated measurement further comprises segmenting the sequence of medical image frames into the plurality of cardiac cycles including the first cardiac cycle and the second cardiac cycle and applying a decision logic to each respective cardiac cycle subphase of each medical image frame of each cardiac cycle. In a sixth example of the method, optionally including one or more or each of the first through fifth examples, the applying the decision logic to determine that the first cardiac cycle is not suitable includes: determining that at least one cardiac cycle subphase of the plurality of cardiac cycle subphases is not included in the first cardiac cycle, determining that a duration of diastole is outside a threshold range of a duration of systole for the first cardiac cycle, and/or determining that the first cardiac cycle has a length that is more than a threshold shorter than an average cycle length of the plurality of cardiac cycles. In a seventh example of the method, optionally including one or more or each of the first through sixth examples, applying the decision logic to determine that the first cardiac cycle is not suitable includes determining that atrial systole is not included in the first cardiac cycle. In an eighth example of the method, optionally including one or more or each of the first through seventh examples, the applying the decision logic to determine that the second cardiac cycle is suitable includes: determining that each cardiac cycle subphase of the plurality of cardiac cycle subphases is included in the second cardiac cycle, determining that a duration of diastole is not outside a threshold range of a duration of systole for the second cardiac cycle, and/or determining that the second cardiac cycle does not have a length that is more than a threshold shorter than an average cycle length of the plurality of cardiac cycles. In a ninth example of the method, optionally including one or more or each of the first through eighth examples, the plurality of cardiac cycle subphases comprises atrial systole, diastasis, rapid inflow, isovolumetric relaxation, ejection, and isovolumetric contraction.

The disclosure also provides support for a system, comprising: a processor, and non-transitory memory storing instructions executable by the processor to: obtain a sequence of medical image frames of a heart of a patient over a plurality of cardiac cycles, each medical image frame in the sequence depicting a same apical view of the heart, segment, based on output from a timing model trained to generate output usable to label each frame of the sequence by cardiac cycle subphase, the sequence of medical image frames into a plurality of sets of medical image frames, each set corresponding to a respective cardiac cycle of the plurality of cardiac cycles, select, based on a suitability of each set of medical image frames for performing an automated measurement, one or more sets of medical image frames, the suitability of each set of medical image frames determined based on each cardiac cycle subphase label of each medical image frame of the sequence, and perform the automated measurement on only the selected one or more sets of medical image frames. In a first example of the system, selecting the one or more sets of medical image frames based on the suitability of each set of medical image frames for performing the automated measurement comprises: entering the sequence of medical image frames as input to the timing model, receiving the output from the timing model, and assigning a respective cardiac cycle subphase to each medical image frame of the sequence based on the output, wherein each respective cardiac cycle subphase is selected from a plurality of cardiac cycle subphases. In a second example of the system, optionally including the first example, the plurality of cardiac cycle subphases comprises atrial systole, diastasis, rapid inflow, isovolumetric relaxation (IVR), ejection, and isovolumetric contraction (IVC). In a third example of the system, optionally including one or both of the first and second examples, selecting the one or more sets of medical image frames based on the suitability of each set of medical image frames for performing the automated measurement further comprises, for a first set of medical image frames of the plurality of sets of medical image frames, the first set of medical image frames corresponding to a first cardiac cycle: determining whether each cardiac cycle subphase of the plurality of cardiac cycle subphases is imaged in the first set of medical image frames, based on the respective cardiac cycle subphase assigned to each medical image frame of the first set of medical image frames, determining whether a length of diastole is outside a threshold range of a length of systole, wherein the length of diastole is determined based on a number of medical image frames of the first set of medical image frames assigned to atrial systole, diastasis, rapid inflow, and IVR, and wherein the length of systole is determined based on a number of medical image frames of the first set of medical image frames assigned to ejection and IVC, and/or determining whether an overall length of the first cardiac cycle represented by the first set of medical image frames is shorter than an average cardiac cycle length by more than a threshold, wherein the overall length of the first cardiac cycle is determined based on a total number of medical image frames in the first set of medical image frames. In a fourth example of the system, optionally including one or more or each of the first through third examples, selecting the one or more sets of medical image frames based on the suitability of each set of medical image frames for performing the automated measurement further comprises: indicating that the first set of medical images is suitable responsive to each cardiac cycle subphase of the plurality of cardiac cycle subphases being imaged in the first set of medical image frames, the length of diastole not being outside the threshold range of the length of systole, and/or the overall length of the first cardiac cycle represented by the first set of medical image frames not being shorter than the average cardiac cycle length by more than the threshold, and in response to the indicating, selecting the first set of medical image frames.

The disclosure also provides support for a method, comprising: obtaining a sequence of medical image frames of a heart of a patient over a plurality of cardiac cycles, each medical image frame in the sequence depicting a same apical view of the heart, entering the sequence of medical image frames as input to a timing model trained to generate output usable to label each frame of the sequence by cardiac cycle subphase, labeling each medical image frame of the sequence based on the output from the timing model to generate a sequence of labeled medical image frames, wherein each medical image frame is labeled with a respective cardiac cycle subphase selected from a plurality of cardiac cycle subphases that includes atrial systole, diastasis, rapid inflow, isovolumetric relaxation (IVR), ejection, and isovolumetric contraction (IVC), segmenting the sequence of labeled medical image frames into a plurality of sets of labeled medical image frames, each set of labeled medical image frames corresponding to a respective cardiac cycle, determining, based on the plurality of sets of labeled medical image frames, a suitability of each set of labeled medical image frames for performing an automated measurement, and performing the automated measurement only on medical image frames of the sequence of medical image frames included in one or more sets of labeled medical image frames determined to be suitable. In a first example of the method, the method further comprises: not performing the automated measurement on medical image frames of the sequence of medical image frames included in one or more sets of labeled medical image frames determined not to be suitable. In a second example of the method, optionally including the first example, determining, based on the plurality of sets of labeled medical image frames, the suitability of each set of labeled medical image frames for performing the automated measurement comprises determining that a first set of labeled medical image frames representing a first cardiac cycle is not suitable based on: determining that at least one cardiac cycle subphase of the plurality of cardiac cycle subphases is not included in the first set of labeled medical image frames, and/or determining that a duration of diastole is outside a threshold range of a duration of systole for the first cardiac cycle. In a third example of the method, optionally including one or both of the first and second examples, determining that the first set of labeled medical image frames is not suitable is further based on determining that the first cardiac cycle has a shorter length than an average cycle length of the plurality of cardiac cycles. In a fourth example of the method, optionally including one or more or each of the first through third examples, determining, based on the plurality of sets of labeled medical image frames, the suitability of each set of labeled medical image frames for performing the automated measurement comprises determining that a first set of labeled medical image frames representing a first cardiac cycle is suitable based on: determining that each cardiac cycle subphase of the plurality of cardiac cycle subphases is included in the first set of labeled medical image frames, and determining that a duration of diastole is not outside a threshold range of a duration systole for the first cardiac cycle.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:

obtaining a sequence of medical image frames of a heart of a patient over a plurality of cardiac cycles, each medical image frame in the sequence depicting a same apical view of the heart;

determining, based on output from a timing model trained to generate output usable to label each frame of the sequence by cardiac cycle subphase, a suitability of each cardiac cycle for performing an automated measurement, wherein determining the suitability of each cardiac cycle includes one or more of determining whether any cardiac cycle subphases are missing and determining whether a duration of diastole is outside a threshold range of a duration of systole for each cardiac cycle;

determining, based on the suitability of each cardiac cycle, that a first cardiac cycle is not suitable, and in response, not performing the automated measurement on medical image frames of the sequence that correspond to the first cardiac cycle; and determining, based on the suitability of each cardiac cycle, that a second cardiac cycle is suitable, and in response, performing the automated measurement on medical image frames of the sequence that correspond to the second cardiac cycle.

2. The method of claim 1, wherein determining, based on output from the timing model trained to generate output usable to label each frame of the sequence by cardiac cycle subphase, the suitability of each cardiac cycle for performing the automated measurement comprises:

entering the sequence of medical image frames as input to the timing model;

receiving the output from the timing model; and assigning a respective cardiac cycle subphase to each medical image frame of the sequence based on the output, wherein each respective cardiac cycle subphase is selected from a plurality of cardiac cycle subphases.

3. The method of claim 2, wherein the output comprises a plurality of prediction curves, each prediction curve corresponding to a respective subphase of the plurality of cardiac cycle subphases and including a probability of each medical image frame of the sequence belonging to that cardiac cycle subphase, and wherein assigning the respective cardiac cycle subphase to each medical image frame of the sequence based on the output comprises assigning the respective cardiac cycle subphase to each medical image frame of the sequence based on the plurality of prediction curves.

4. The method of claim 2, wherein the output comprises a plurality of prediction curves, each prediction curve corresponding to a respective event of a plurality of events and including a probability of each medical image frame of the sequence belonging to that event, and wherein assigning the respective cardiac cycle subphase to each medical image frame of the sequence based on the output comprises assigning the respective cardiac cycle subphase to each medical image frame of the sequence based on the plurality of prediction curves.

5. The method of claim 4, wherein each event of the plurality of events signals a transition to a new cardiac cycle subphase, and wherein assigning the respective cardiac cycle subphase to each medical image frame of the sequence based on the plurality of prediction curves comprises identifying which medical image frames of the sequence correspond to each event by identifying peaks in the plurality of prediction curves, and assigning the respective cardiac cycle subphase to each medical image frame of the sequence based on proximity to the medical image frames of the sequence that correspond to each event.

6. The method of claim 2, wherein determining, based on output from the timing model trained to generate output usable to label each frame of the sequence by cardiac cycle subphase, the suitability of each cardiac cycle for performing the automated measurement further comprises segmenting the sequence of medical image frames into the plurality of cardiac cycles including the first cardiac cycle and the second cardiac cycle and applying a decision logic to each respective cardiac cycle subphase of each medical image frame of each cardiac cycle.

7. The method of claim 6, wherein the applying the decision logic to determine that the first cardiac cycle is not suitable includes two or more of:

determining that at least one cardiac cycle subphase of the plurality of cardiac cycle subphases is not included in the first cardiac cycle and thus is missing, determining that a duration of diastole is outside a threshold range of a duration of systole for the first cardiac cycle, and determining that the first cardiac cycle has a length that is more than a threshold shorter than an average cycle length of the plurality of cardiac cycles.

8. The method of claim 7, wherein applying the decision logic to determine that the first cardiac cycle is not suitable includes determining that atrial systole is not included in the first cardiac cycle.

9. The method of claim 6, wherein the applying the decision logic to determine that the second cardiac cycle is suitable includes two or more of:

determining that each cardiac cycle subphase of the plurality of cardiac cycle subphases is included in the second cardiac cycle and thus no cardiac cycle subphase is missing, determining that a duration of diastole is not outside a threshold range of a duration of systole for the second cardiac cycle, and determining that the second cardiac cycle does not have a length that is more than a threshold shorter than an average cycle length of the plurality of cardiac cycles.

10. The method of claim 2, wherein the plurality of cardiac cycle subphases comprises atrial systole, diastasis, rapid inflow, isovolumetric relaxation, ejection, and isovolumetric contraction, and wherein the suitability of each cardiac cycle is determined based on each cardiac cycle subphase of each medical image frame of the sequence.

11. A system, comprising:

a processor; and non-transitory memory storing instructions executable by the processor to:

obtain a sequence of medical image frames of a heart of a patient over a plurality of cardiac cycles, each medical image frame in the sequence depicting a same apical view of the heart;

segment, based on output from a timing model trained to generate output usable to label each frame of the sequence by cardiac cycle subphase, the sequence of medical image frames into a plurality of sets of medical image frames, each set corresponding to a respective cardiac cycle of the plurality of cardiac cycles;

determine, by applying a decision logic to each set of medical image frames, a suitability of each set of medical image frames for performing an automated measurement, the suitability of each set of medical image frames determined based on each cardiac cycle subphase label of each medical image frame of the sequence;

select, based on the suitability of each set of medical image frames for performing the automated measurement, one or more sets of medical image frames; and perform the automated measurement on only the selected one or more sets of medical image frames.

12. The system of claim 11, wherein selecting the one or more sets of medical image frames based on the suitability of each set of medical image frames for performing the automated measurement comprises:

entering the sequence of medical image frames as input to the timing model;

receiving the output from the timing model; and assigning a respective cardiac cycle subphase to each medical image frame of the sequence based on the output, wherein each respective cardiac cycle subphase is selected from a plurality of cardiac cycle subphases.

13. The system of claim 12, wherein the plurality of cardiac cycle subphases comprises atrial systole, diastasis, rapid inflow, isovolumetric relaxation (IVR), ejection, and isovolumetric contraction (IVC).

14. The system of claim 13, wherein applying the decision logic further comprises, for a first set of medical image frames of the plurality of sets of medical image frames, the first set of medical image frames corresponding to a first cardiac cycle:

determining whether each cardiac cycle subphase of the plurality of cardiac cycle subphases is imaged in the first set of medical image frames, based on the respective cardiac cycle subphase assigned to each medical image frame of the first set of medical image frames;

determining whether a length of diastole is outside a threshold range of a length of systole, wherein the length of diastole is determined based on a number of medical image frames of the first set of medical image frames assigned to atrial systole, diastasis, rapid inflow, and IVR, and wherein the length of systole is determined based on a number of medical image frames of the first set of medical image frames assigned to ejection and IVC; and/or determining whether an overall length of the first cardiac cycle represented by the first set of medical image frames is shorter than an average cardiac cycle length by more than a threshold, wherein the overall length of the first cardiac cycle is determined based on a total number of medical image frames in the first set of medical image frames.

15. The system of claim 14, wherein selecting the one or more sets of medical image frames based on the suitability of each set of medical image frames for performing the automated measurement further comprises:

indicating that the first set of medical images is suitable responsive to each cardiac cycle subphase of the plurality of cardiac cycle subphases being imaged in the first set of medical image frames, the length of diastole not being outside the threshold range of the length of systole, and/or the overall length of the first cardiac cycle represented by the first set of medical image frames not being shorter than the average cardiac cycle length by more than the threshold;

and in response to the indicating, selecting the first set of medical image frames.

16. A method, comprising:

obtaining a sequence of medical image frames of a heart of a patient over a plurality of cardiac cycles, each medical image frame in the sequence depicting a same apical view of the heart;

entering the sequence of medical image frames as input to a timing model trained to generate output usable to label each frame of the sequence by cardiac cycle subphase;

labeling each medical image frame of the sequence based on the output from the timing model to generate a sequence of labeled medical image frames, wherein each medical image frame is labeled with a respective cardiac cycle subphase selected from a plurality of cardiac cycle subphases that includes atrial systole, diastasis, rapid inflow, isovolumetric relaxation (IVR), ejection, and isovolumetric contraction (IVC);

segmenting the sequence of labeled medical image frames into a plurality of sets of labeled medical image frames, each set of labeled medical image frames corresponding to a respective cardiac cycle;

determining, based on the plurality of sets of labeled medical image frames, a suitability of each set of labeled medical image frames for performing an automated measurement, including determining that a first set of labeled medical image frames representing a first cardiac cycle is suitable based on: determining that each cardiac cycle subphase of the plurality of cardiac cycle subphases is included in the first set of labeled medical image frames, and determining that a duration of diastole is not outside a threshold range of a duration systole for the first cardiac cycle; and performing the automated measurement only on medical image frames of the sequence of medical image frames included in one or more sets of labeled medical image frames determined to be suitable.

17. The method of claim 16, further comprising not performing the automated measurement on medical image frames of the sequence of medical image frames included in one or more sets of labeled medical image frames determined not to be suitable.

18. The method of claim 16, wherein determining, based on the plurality of sets of labeled medical image frames, the suitability of each set of labeled medical image frames for performing the automated measurement comprises determining that a second set of labeled medical image frames representing a second cardiac cycle is not suitable based on:

determining that at least one cardiac cycle subphase of the plurality of cardiac cycle subphases is not included in the second set of labeled medical image frames, and/or determining that a duration of diastole is outside a threshold range of a duration of systole for the second cardiac cycle.

19. The method of claim 18, wherein determining that the first set of labeled medical image frames is not suitable is further based on determining that the first cardiac cycle has a shorter length than an average cycle length of the plurality of cardiac cycles.

* * * * *